United States Patent [19]

Scantlebury et al.

[11] Patent Number: 5,032,445
[45] Date of Patent: Jul. 16, 1991

[54] METHODS AND ARTICLES FOR TREATING PERIODONTAL DISEASE AND BONE DEFECTS

[75] Inventors: Todd V. Scantlebury; Jeanne B. Ambruster; Suzanne Motsinger; Daniel F. Davidson; William R. Hardwick, all of Flagstaff; Stephen E. Campbell, Cave Creek, all of Ariz.

[73] Assignee: W. L. Gore & Associates, Newark, Del.

[21] Appl. No.: 333,289

[22] Filed: Apr. 5, 1989

Related U.S. Application Data

[63] Continuation-in-part of Ser. No. 845,878, Apr. 30, 1986, abandoned, which is a continuation-in-part of Ser. No. 628,308, Jul. 6, 1984, abandoned.

[51] Int. Cl.$^5$ .................. A61G 17/02; A61F 13/00; B32B 3/12
[52] U.S. Cl. .................. 428/158; 428/76; 428/105; 428/113; 428/213; 428/192; 428/318.4; 428/343; 428/292; 433/80; 433/215; 604/890.1
[58] Field of Search .................. 433/80, 215, 175; 424/27, 28; 604/890, 891, 892; 428/106, 105, 76, 213, 113, 158, 292, 192, 304.4, 318.4, 343

[56] References Cited

U.S. PATENT DOCUMENTS

| | | | |
|---|---|---|---|
| 2,748,781 | 6/1956 | Collat | 132/93 |
| 2,991,224 | 7/1961 | Bell | 428/28 |
| 3,386,440 | 6/1968 | Cohen | 424/28 |
| 3,589,011 | 6/1971 | Sneer | 32/10 |
| 3,754,332 | 8/1973 | Warren, Jr. | 428/28 |
| 3,855,638 | 12/1974 | Pilliar | 3/1 |
| 3,863,344 | 2/1975 | Pillet | 32/10 A |
| 3,879,767 | 4/1975 | Stubstad | 3/1 |
| 3,909,852 | 10/1975 | Homsey | 3/1.9 |
| 3,953,566 | 4/1976 | Gore | 264/505 |
| 3,971,134 | 7/1976 | Bokros | 32/10 A |
| 3,971,679 | 7/1976 | Homsey | 156/196 |
| 4,007,494 | 2/1977 | Sauer | 3/1.9 |
| 4,020,558 | 5/1977 | Cournut et al. | 604/892 |
| 4,039,653 | 8/1977 | De Foney et al. | 424/28 |
| 4,136,162 | 1/1979 | Fuchi et al. | 424/27 |
| 4,175,326 | 11/1979 | Goodson | 433/80 |

(List continued on next page.)

FOREIGN PATENT DOCUMENTS

| | | |
|---|---|---|
| 0089782 | 8/1983 | European Pat. Off. |
| 1499912 | 3/1967 | France |
| 2306672 | 5/1973 | France |
| WO90/07308 | 7/1990 | PCT Int'l Appl. |
| 1390445 | 4/1980 | United Kingdom |
| 1602932 | 11/1981 | United Kingdom |

OTHER PUBLICATIONS

J. Periodontol., vol. 51:110 (1980).
Periodontics, vol. 4:71 (1966).
J. Periodontol., vol. 54:29 (1983).
J. Clin. Periodontol. 1974:1:75.
J. Periodontal Res. vol. 18:643 (1983).
J. Periodonol. vol. 51:652 (1980).

(List continued on next page.)

Primary Examiner—Ellis P. Robinson
Assistant Examiner—Donald J. Loney

[57] ABSTRACT

A method for treatment of periodontal disease is disclosed. The gingival tissue is separated from the tooth surface in an area where periodontal disease is present. A biocompatible, porous material such as expanded polytetrafluoroethylene capable of supporting ingrowth of gingival connective tissue and preventing apical migration of gingival epithelium is placed in a laminar relationship to a portion of the perimeter of the tooth surface. The gingival tissue is repositioned around the tooth and in contact with the porous material, with the porous material positioned between the gingival tissue and the tooth. Articles for the treatment of periodontal disease are also disclosed. One article comprises a first portion which is capable of supporting ingrowth of gingival connective tissue and preventing apical migration of gingival epithelium and a second portion which is impermeable to oral tissues and bacteria.

77 Claims, 9 Drawing Sheets

U.S. PATENT DOCUMENTS

| | | | |
|---|---|---|---|
| 4,187,390 | 2/1980 | Gore | 174/102 R |
| 4,195,409 | 4/1980 | Child | 433/175 |
| 4,244,689 | 7/1980 | Ashman | 433/175 |
| 4,252,525 | 2/1981 | Child | 433/173 |
| 4,321,914 | 3/1982 | Begovac et al. | 128/887 |
| 4,400,833 | 8/1983 | Kurland | 3/1 |
| 4,492,390 | 2/1984 | Farris et al. | 281/31 |
| 4,531,916 | 7/1985 | Scantlebury et al. | 433/173 |
| 4,752,294 | 6/1988 | Lundgren | 623/11 |

OTHER PUBLICATIONS

J. Clin. Periodontol. vol. 11:494 (1984).

Prichard, John, "The Roentgenographic Depiction of Periodontal Disease".

Robert Langer & Nikolaos Peppas, "Chemical and Physical Structure of Structure of Polymers as Carriers for Controlled Release of Bioactive Agents: A Review", 4022 Journal of Macromolecular Science Reviews on Macromolecular Chemistry and Physics C23 (1983) No. 1.

Murray et al., "Experimental and Clinical Study of New Growth of Bone in a Cavity", American Journal of Surgery vol. 93, Mar. (1957).

Linghorne, "The Sequence of Events in Osteogenesis As Studied in Polyethylene Tubes", Annals New York Academy of Sciences 85:455-460 1960.

Melcher et al., "Protection of the Blood Clot in Healing Circumscribed Bone Defects", Journal of Bone and Joint Surgery vol. 44B, No. 2 1962, pp. 424-430.

Gongloff et al., "Use of Collagen Tubes for Implantation of Hydroxylapatite", Journal of Maxillofacial Surgery 43:570-573 (1985).

Dahlin et al., "Healing of Bone Defects by Guided Tissue Regeneration", Surgery vol. 81, No. 5 pp. 672-676 (1988).

Aukhil et al., "Guided Tissue Regeneration", Journal Periodontal vol. 57, No. 12 pp. 727-734 (1986).

Magnusson et al., "Connective Tissue Attachment Formation Following Exclusion of Gingival Connective Tissue and Epithelium During Healing", Journal of Periodontal Research vol. 20, pp. 201-208 (1985).

Pitaru et al., "Partial Regeneration of Periodontal Tissue Using Collagen barriers", J. Periodontal vol. 59, No. 6, pp. 380-386 (1988).

Velasco et al., "A Study of Autologous Cancellous Bone Particles in Long Bone Discontinuity Defects", Clinical Orthopaedics and Related Research No. 177, pp. 264-273 (1983).

Zander, H. A., Polson, A. M. and Heiil, C. D.: Goals of Periodontal Therapy, J. Periodontal 47:261, 1976.

Melcher, A. H.: On the Repair Potential of Periodontal Tissues, J. Periodontal 47:256, 1976.

McCulloch, C. A. G., and Melcher, A. H.: Cell Density and Cell Generation in the Periodontal Ligament of Mice, Am. J. Anat. 167:43, 1983.

Aukil, I., Petterson, E. and Suggs, C.: Periodontal Wound Healing in the Absence of Periodontal Ligament Cells, J. Periodontal 58:71, 1987.

Nyman, S, Gottlow, J., Karring, T. and Lindhe, J.: the Regenerative Potential of the Periodontal Ligament, An Experimental Study in the Monkey, J. Clin. Periodontal 9:257, 1982.

Gottlow, J., Nyman, S., Karring, T. and Lindhe, J.: New Attachment Formation as the Result of Controlled Tissue Regeneration, J. Clin. Periodontal 11:494, 1984.

Caton, J. G., Defuria, E. L., Polson, A. M. and Nyman, S.: Periodontal Regeneration Via Selective Cell Repopulation, J. Periodontal 58:546, 1987.

Quiones, C. R., Caton, J. G., Mota, L. F., Polson, A. M. and Wagener, C. J. Evaluation of a Synthetic Biodegradable barrier to Facilitate Guided Tissue Regeneration, J. Dent. Res. 69: Special Issue, 1990, Abstract #1336.

Caton, J. G., Frantz, B, Greenstein, G., Hoffman, P., Polson, A. M., and Zappa, O: Synthetic Biodegradable Barrier for Regeneration in Human Periodontal Defects, J. Dent. Res. 69: Special Issue, 1990, Abstract #1335.

METHODS AND ARTICLES FOR TREATING PERIODONTAL DISEASE AND BONE DEFECTS

This application is a continuation-in-part application of Ser. No. 845,878 filed Apr. 30, 1986 now abandoned which was a continuation-in-part of application Ser. No. 628,308 filed July 6, 1984 now abandoned.

BACKGROUND

The present invention relates to methods and articles for treatment of periodontal disease, in particular to methods and articles for inhibiting periodontal pocket formation and healing periodontal defects. The present invention also provides methods and articles for treatment of bony defects. Although examples described herein relate to bone defects in the mouth, similar treatment is applicable throughout the human body.

Periodontal disease is a disease of the periodontium, the tissues that invest and support the teeth as shown in FIG. 1. These tissues include: Gingiva 1, the soft gum tissue of the mouth; gingival epithelium 2, the protective surface layer of the gingiva which seals against the tooth where the tooth passes into the oral cavity; the cementum (not designated in FIG. 1), a natural adhesive covering the tooth root; alveolar bone 3, the bone of the jaw surrounding the tooth root; and the periodontal ligament 4, connective tissue which suspends and supports the tooth between alveolar bone and the tooth root.

The gingival tissue surrounding a healthy adult tooth, as illustrated in FIG. 2, forms a sulcus 5 where it attaches to the tooth. In the early stages of periodontal disease, the bacteria break down the attachment of the gingival epithelium to the tooth, forcing the epithelium to reattach apically (toward the root) away from infected tissue. Because the tissue is compromised by disease, the new attachment is weak. Further infection progressively moves the attachment apically until the tooth is surrounded by a loose sleeve of diseased gingiva creating a pocket which is much deeper than the normal sulcus. As depicted in FIG. 3, the loose sleeve, called a periodontal pocket 6, is difficult to clean because a tooth brush and floss cannot reach the bacteria and plaque which accumulate within the pocket. As disease extends the periodontal pocket, the cementum, periodontal ligament, and supporting alveolar bone are destroyed, leaving a periodontal defect 7 filled with plaque and bacteria. Eventually the loss of the supporting periodontium leads to loss of the tooth.

Periodontal disease is the most common disease known to man. It is reported in the literature that it affects 75 percent of the adult population and is the major reason for tooth loss after the age of 35, and that fifty-five million teeth are lost to the disease each year in the United States.

Conventional treatment of periodontal defects consists of attempts to surgically alter the periodontal pocket morphology or obtain coronal (toward the crown) reattachment of the gingiva to the tooth. One prior art method alters the periodontal pocket morphology, creating a normally-shaped pocket at a site apical to the original attachment. This is accomplished by cutting away the coronal gingival tissue of a periodontal pocket and, if necessary, reshaping the underlying bone, to create a periodontal pocket similar in depth to a normal sulcus so that regular oral hygiene might be used to maintain the attachment of the gingiva to the tooth. This treatment does not recreate the coronal attachment of gingiva to the tooth maintained before the diseased condition and does not replace periodontium lost to the disease.

In another conventional treatment known as a gingival flap procedure, one or more flaps of gingival tissue are dissected away from the tooth. After the tooth is thoroughly cleaned by scaling or curetting; the flaps are reapposed to the tooth, sometimes incorporating gingival grafts from other portions of the mouth. However, reattachment of gingiva to a tooth surface that has been diseased is difficult to obtain using this procedure. Gingival epithelium migrates rapidly along the tooth root surface toward the apex of the tooth. Because bone and the periodontal ligament heal much more slowly than the migrating epithelium, the epithelium often migrates apically back to the presurgical level, recreating a periodontal pocket similar in dimension to the pocket before treatment. Although the flap procedure is commonly used by clinicians, it is mostly successful with three wall defects (referring to the number of bony walls left surrounding a defect); less successful with two wall defects, and not at all successful with one wall defects (Ellegaard, B., Karring, T. and Loe, H. "New periodontal attachment procedure based on retardation of epithelial migration," J. Clinical Periodontology 74:1:75-88).

Historically, investigators have attempted to improve upon the treatment of periodontal disease by encouraging the attachment of gingival tissue to the tooth, speeding the healing of gingival tissue from a healing defect site. By etching the tooth root surface with acids, some researchers have attempted to cause the gingival connective tissue (the highly vascular connective structure of the gingiva) to attach to the tooth, thus stopping the apical migration of gingival epithelium. Other researchers have attempted to fill bony defects with autogenous bone or artificial bone substitutes such as hydroxylapatite or tricalcium phosphate so that the bony portion of the defect might heal despite the rapid apical spread of epithelium. In another treatment, foils or other membranes into which gingival tissue cannot penetrate are used to separate the gingival tissue from the healing defect. In this method, the epithelium migrates apically along one side of the membrane or foil, while the defect heals on the opposite side of the membrane.

Previous attempts to correct periodontal defects with synthetic materials have not provided for the attachment of gingival tissue to the tooth while controlling the apical migration of epithelium. For this reason, these techniques have met with only limited success. Ideally periodontal disease should be treated by obtaining an attachment of gingival tissue to the tooth which will halt the apical migration of epithelium near the level maintained before the disease. The defect apical to the gingival attachment can then be healed in by the appropriate periodontal tissues.

A bony defect is any unnatural or irregular anatomy of the bone structure, particularly where bone is missing from the natural anatomy. Bone defects are commonly found in the oral cavity including the jaw bone, and are often the result of traumatic injury to the teeth and bone, disease affecting pulp canals of the teeth, periodontal disease, tooth root fractures, tumors or cancer, or congenital defects.

These defects may be functional or aesthetic in nature and have been treated in the past by grafting either natural or synthetic materials to increase tissue volume.

The natural grafting materials include iliac, rib, or oral bone harvested from the patient who will receive the graft (i.e. autogenous), cortical or cancellous bone harvested from an individual different from the patent (i.e., allogenous), or cortical or cancellous bone harvested from a different mammalian species (i.e. xenogenous). Synthetic materials include particles or blocks of either solid or porous hydroxylapatite, particles or blocks of synthetic polymers such as poly (methylmethacrylate) or processed collagenous material usually obtained from a bovine source.

There are two major difficulties associated with the use of the above materials. First, none of the above-mentioned materials predictably result in resolution of the bony defect with viable bone tissue. Autogenous iliac grafts result in the most predictable bone healing, but require a painful surgical procedure to harvest the iliac graft material.

After surgical placement of any of the above mentioned graft materials into a bone defect, bone cells and fibrous connective tissue cells compete to fill the void space within the graft material or to replace the graft material as it resorbs. Because fibrous connective tissue can grow and form faster than bone tissue, the above-mentioned graft materials may attach or be partly ingrown with bone; however, the majority of healing is accomplished by ingrowth of soft connective tissue. In addition, with particulate materials, the particles tend to migrate over time through the soft tissue beyond the margins of the bone defect thereby reducing or minimizing therapeutic results.

The second major problem is that all of the above-mentioned materials are prone to either dehiscence of the suture line due to stretching the gingival tissue over them during closure of the surgical site or perforation of the graft material through the gingival tissue at some point after initial healing has occurred. In either case, exposure of the graft material occurs with subsequent infection and loss of graft material.

SUMMARY OF THE INVENTION

The present invention, in one embodiment, provides a method for treatment of periodontal disease comprising: (a) separating the gingival tissue from a tooth surface in an area where periodontal disease is present; (b) fixing a biocompatible, porous material, capable of supporting ingrowth of gingival connective tissue and preventing apical migration of gingival epithelium, in a laminar relationship to (i.e., parallel and in intimate contact with) a portion of the perimeter of the tooth; and (c) repositioning the gingival tissue around the tooth and in contact with the porous material, with at least a portion of the porous material positioned between the gingival tissue and the tooth.

The present invention further provides an article for the treatment of periodontal disease comprising a length of porous material capable of supporting ingrowth of gingival connective tissue and preventing the apical migration of gingival epithelium, said length having a biocompatible non-porous backing on a side capable of being placed in laminar relationship to a tooth surface. Additionally, the present invention provides an article for the treatment of periodontal disease comprising a porous material capable of supporting gingival connective tissue ingrowth and preventing apical migration of gingival epithelium, said length having at least one filament attached to each of two opposite ends serving to tie said porous material around a tooth.

The invention involves placement of a porous material between the tooth surface and gingival tissue in an area in which periodontal disease has caused the attachment of the gingival epithelium to the tooth to migrate apically. Upon placement of the porous material in laminar relationship to a portion of the perimeter of the tooth surface, the gingival tissue is repositioned around the tooth, resulting in the porous material being located between the gingival tissue and the tooth. During healing the porous material fills with gingival connective tissue thus halting the apical downgrowth of gingival epithelium. As such, the area which previously comprised the periodontal pocket fills in with healthy periodontal tissue.

Moreover, it has been found that the use of an article wherein a first surface of the article is a porous material capable of supporting the ingrowth of gingival connective tissue and preventing the apical migration of gingival epithelium and a second surface of the article is substantially impermeable to oral tissues in a method similar to that set forth above also results in successful treatment of periodontal disease. Thus, the present invention also provides a method for the treatment of periodontal disease comprising: (a) temporarily separating the gingival tissue from a tooth surface in an area where periodontal disease is present; (b) fixing an article in a laminar relationship to a portion perimeter of a tooth surface, wherein the article comprises a member having first and second juxtaposed surfaces meeting at a boundary wherein the boundary is capable of at least partially encircling the perimeter of the tooth to be treated, said first surface comprising a porous, biocompatible material capable of supporting the ingrowth of gingival connective tissue and capable of preventing the apical migration of gingival epithelium, said first surface further configured so as to surround a portion of the perimeter of the tooth immediately apical to the desired sulcus line with the porous surface abutting the gingival connective tissue, and said second surface being substantially impermeable to oral tissues and configured so as to surround at least a portion of the perimeter of the tooth apical to the first surface, said second surface positioned so that after healing at least a portion of the first surface is exposed to gingival epithelial tissue in the area of the desired sulcus line and said second surface abutting the gingival connective tissue and (c) reattaching the gingival tissue around the tooth and in contact with the article.

For use in the method of this latter embodiment, the present invention also provides an article for the treatment of periodontal disease by promoting gingival tissue attachment about a desired sulcus line. The article comprises a member having first and second juxtaposed surfaces meeting at a boundary wherein said boundary is capable of at least partially encircling the perimeter of a tooth to be treated. The first surface is formed by a porous, biocompatible material capable of supporting ingrowth of gingival connective tissue and preventing the apical migration of gingival epithelium and configured so as to surround at least a portion of the perimeter of the tooth immediately apical to the desired sulcus line, with the porous surface abutting the gingival connective tissue. The said second surface is formed by a material substantially impermeable to oral tissues and configured so as to surround at least a portion of the perimeter of the tooth apical to the first surface so that after healing the first surface is exposed to gingival epithelial tissue in the area of the desired sulcus line, the impermeable surface abutting the gingival connective tissue. Although the accompanying drawings show certain preferred shapes and geometries of the article of this invention, they are not to be taken to limit the scope of the appended claims.

It has also been found that the invention provides an article and method for successful treatment of bony defects particularly in the jaw bone of the mouth. The method of treatment involves placement of the article over the bony defect thus creating a space between the article and the bone in the region of the defect into which bone cells proliferate. The article itself protects the defect space thus created from epithelium, fibrous connective tissue, and bacteria all of which would normally be detrimental to bone tissue healing within the defect region. The article thus allows predictable resolution of bony defects even in the event of exposure of the article to the oral or outside environment through dehiscence of the suture line, perforation of the overlying soft tissue or inability to obtain primary or complete closure of the soft tissue.

One embodiment is similar to that described above for the treatment of periodontal disease wherein a first porous layer having a surface capable of supporting ingrowth or attachment of fibrous connective tissue is arranged in laminar relationship with a second backing layer, which is substantially impermeable or incapable of penetration by tissue and bacteria through the layer. Here, the first porous layer allows fibrous connective tissue ingrowth into the porous material or attachment along the outer surface of the porous material to inhibit or retard epithelial migration. The backing layer substantially prevents undesirable tissue and bacteria from entering the space of the bony defect and allows desirable bone cells to proliferate in the space created by the layered article.

A second embodiment for treatment of bony defects comprises a member having a first surface that is formed from a porous material capable of supporting the ingrowth of fibrous connective tissue thus preventing or retarding the migration of epithelium and further having a second surface juxtaposed to and surrounded by the first surface formed from a material which is substantially impermeable to oral tissues and bacteria. The invention involves placement of the integral two-part member over the bony alveolar ridge defect with the second surface of the article substantially impermeable to oral tissues and bacteria over the defect area and the first surface of porous material capable of supporting ingrowth of fibrous connective tissue peripheral to the defect area.

It is to be understood that both the foregoing general description and the following detailed description are exemplary and explanatory only and are not restrictive of the invention, as claimed.

Additional advantages of the invention will be set forth in part in the detailed description which follows, and in part will be obvious from the description or may be learned by practice of the invention. The advantages of the invention may be realized and attained by means of the instrumentalities and combinations particularly pointed out in the appended claims.

The accompanying drawings, which are incorporated in and constitute a part of the specification, illustrate six exemplary embodiments of the invention and, together with the description, serve to explain the principles of the invention.

DETAILED DESCRIPTION OF THE PREFERRED EMBODIMENTS

Figure 1:
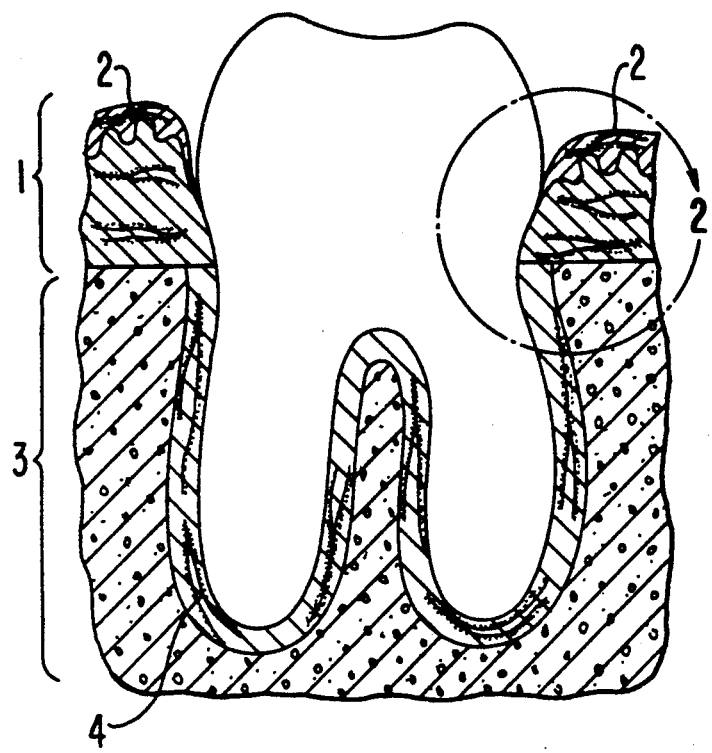
FIG. 1 is a mesial-distal (parallel with jawbone ridge) cross-sectional view of a healthy adult tooth and periodontium.
Figure 2:
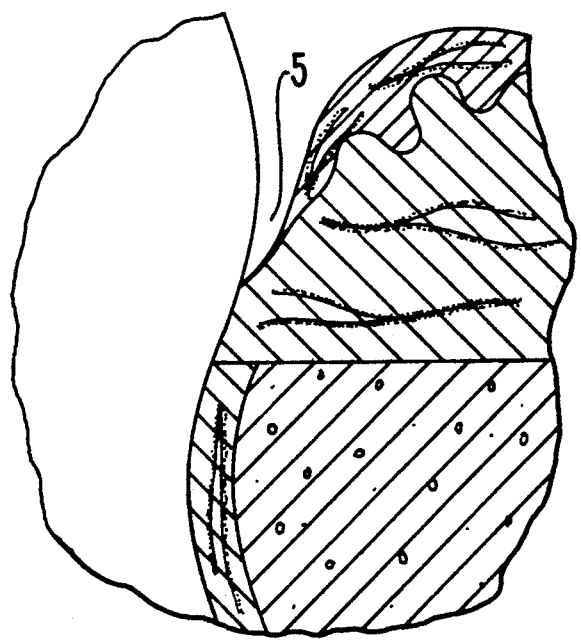
FIG. 2 is a close-up view of the gingival sulcus of FIG. 1.
Figure 3:
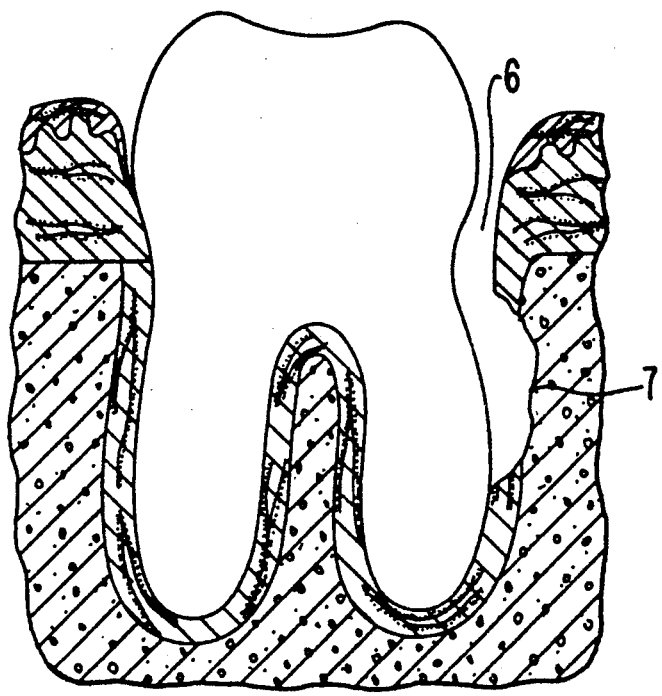
FIG. 3 is a mesial-distal cross-sectional view of a periodontally diseased tooth with periodontal pocket and defect.

Reference will now be made in detail to the present preferred embodiments of the invention, examples of which are illustrated in the accompanying drawings.

The present invention in part provides a method for treatment of periodontal disease which comprises:

(a) separating the gingival tissue from a tooth surface in an area where periodontal disease is present;

(b) fixing a biocompatible, porous material, capable of supporting ingrowth of gingival connective tissue and preventing apical migration of gingival epithelium, in a laminar relationship to a portion of the perimeter of the tooth; and (c) repositioning the gingival tissue around the tooth and in contact with the porous material, with at least a portion of the porous material positioned between the gingival tissue and the tooth.

Preferably, a periodontally diseased tooth is prepared for repair by exposing all diseased portions of the tooth and periodontium. For example, one or more buccal (toward cheek) or lingual (toward the tongue) flaps of gingiva can be reflected away from the tooth root and surrounding bone. The exposed defect can then be cleaned by conventional periodontic techniques such as scaling or curetting. Topical antibiotics may be applied to the diseased sites to discourage the population of bacteria.

The porous material is placed against the tooth surface and should extend coronally to the level at which repair of the defect is desired to occur. Preferably the porous material is placed to the level on the tooth just apical of where it is desired for the gingival epithelium (sulcus) to end.

The porous material may be wrapped around the entire perimeter of the tooth. It is preferably placed around the portion of the tooth's perimeter where periodontal tissue attachment has been lost to disease. The porous material may be placed flat against the tooth surface. Preferably the porous material extends out from the tooth surface to cover any bony defects surrounding the tooth.

The porous material should be closely apposed to the tooth surface so that gingival epithelium cannot pass between the porous material and the tooth surface. The porous material may simply be placed between the gingival tissue and the tooth surface or it may be secured to the tooth surface.

The porous material may be secured to the tooth surface by adhering the material to the tooth with suitable dental adhesives. A suitable dental adhesive is non-toxic to surrounding tissues, is capable of forming an adhesive bond in an open oral environment, will remain for a sufficient amount of time to allow the defect to be repaired, and is capable of forming a bond between a porous surface and a tooth surface. Dental adhesives include, but are not limited to, zinc euginol, zinc phosphate, zinc silicophosphate, acrylic, glass ionomer, silicate and polycarboxylate cements.

The porous material may also be secured in place around the tooth through the use of sutures or filaments. Sutures may be used to lash the porous material to surrounding tissue and, thereby, hold it snugly against the tooth. Suture material may also be used to join the ends of porous material together to secure the porous material around the tooth. A filamentous material may be attached to the ends of the porous material and used to tie the porous material around the tooth. Such suture materials or filamentous materials must be biocompatible., i.e., must be materials which do not adversely affect oral tissue. Additionally, the sutures or filamentous materials should not act as a conduit for bacterial invasion nor should they resorb until sufficient time has elapsed to allow periodontal tissues to fill in the defect. A preferred suture material, which may also be used as a filament is any small diameter resorbable suture such as 5-0 Dexon ®, available from Davis and Geck, Inc.

Figure 4:
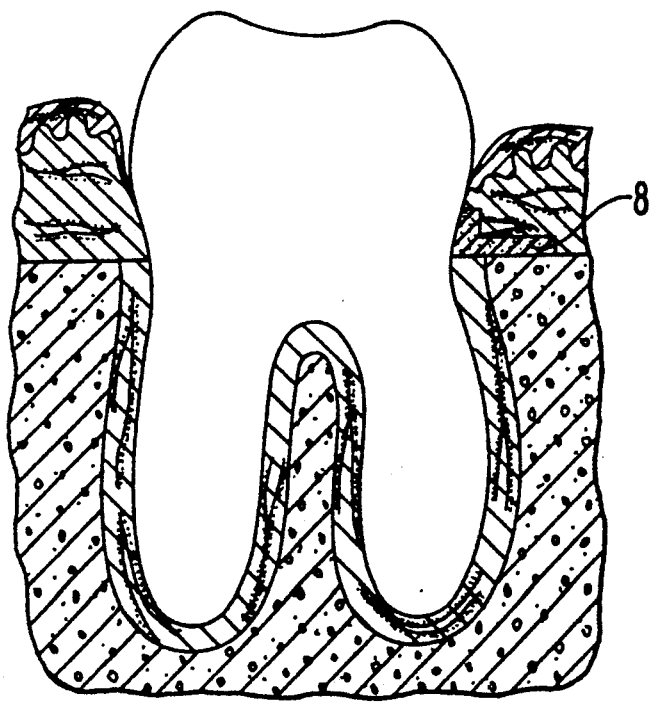
FIG. 4 is a mesial-distal cross-sectional view of the diseased tooth of FIG. 3 repaired with the present invention.

Gingival tissue is positioned against the porous material so that the porous material separates some portion of the gingiva from the tooth surface. The coronal portion of the porous material may extend coronal to the gingival tissue. Preferably, as depicted in FIG. 4, the porous material 8 is completely covered with gingival tissue, leaving no portion of the porous material exposed to the oral cavity.

The porous material may remain in the mouth for the life of the patient. Alternatively, the porous material may be removed after a time sufficient for the periodontal tissues to fill the defect and attach to the tooth surface.

The porous material should be made from biocompatible materials. The porous material must also allow for the rapid ingrowth of gingival connective tissue to inhibit the apical migration of gingival epithelium along the surface of the material. Preferably the porous material is soft and flexible so that it will conform to the curvature of the tooth and surrounding bone and not cause tissue necrosis in the tissues against which it is placed. Suitable biocompatible materials which can be made porous include, but are not limited to, silicones, polyurethanes, polyethylenes, polysulfones, polyacrylics, polycarboxylates, polyesters, polypropylenes, poly(hydroxyethylmethacrylates), and perfluorinated polymers, such as fluorinated ethylene propylene, and polytetrafluoroethylene.

The above-mentioned may be made porous by any techniques known to those of ordinary skill in the art which will render the materials capable of supporting gingival connective tissue ingrowth while preventing apical migration of gingival epithelium. Such techniques include, but are not limited to, sintering carefully controlled sizes of beads; combining the materials with a partially resorbable implant that would resorb or could be resorbed, in vivo or in vitro, to leave a porous surface; weaving or knitting fibers together to form a fabric-like material; or using a foaming agent during processing to cause bubbles to form and leave pores as the material hardens.

The porous material may be treated or filled with biologically active substances such as antibiotics, fibrin, thrombin, and collagen. These substances may enhance connective tissue formation within the porous material and inhibit infection during healing.

The porous material may be backed with a non-porous material on the side of the porous material which juxtaposes the tooth surface. The non-porous material aids in retaining the open, porous structure of the porous material. The non-porous material would also aid in sealing the porous material against the tooth surface by conforming to the irregularities of the surface. Suitable non-porous materials include, but are not limited to, the porous materials listed above, and combinations thereof.

The non-porous material can also be used to secure the porous material to the tooth surface by serving as a surface which bonds to a tooth-adhering adhesive. In this embodiment, a suitable dental adhesive, as set forth above, may be applied to the tooth or the non-porous side of the porous material before adhering the material onto the tooth. In another embodiment, one component of a multi-component adhesive may be incorporated into the non-porous material. The adhesive or the remaining components of the adhesive are introduced immediately before the material is adhered to the tooth.

The porous material of the preferred embodiment is expanded polytetrafluoroethylene (expanded PTFE). Expanded PTFE is an extremely inert and biocompatible material with a history of medical implant use. U.S. Pat. Nos. 3,953,566 and 4,187,390, the disclosures of which are incorporated herein by reference, teach methods for producing expanded PTFE and characterize its porous structure. The porous structure of expanded PTFE is further illustrated in FIG. 5. The microstructure of expanded PTFE is a three-dimensional matrix of nodes 9, connected by fibrils 10.

The pore size of expanded PTFE can be characterized by determining the bubble point and the mean flow pressure of the material. Bubble point and mean flow pressure are measured according to the American Society for Testing and Materials Standard F316-80 using ethanol.

The density of expanded PTFE determines the amount of void space in the material which may become ingrown with connective tissue. The density of expanded PTFE is the ratio of the mass of a given sample of expanded PTFE to its volume.

Figure 5:
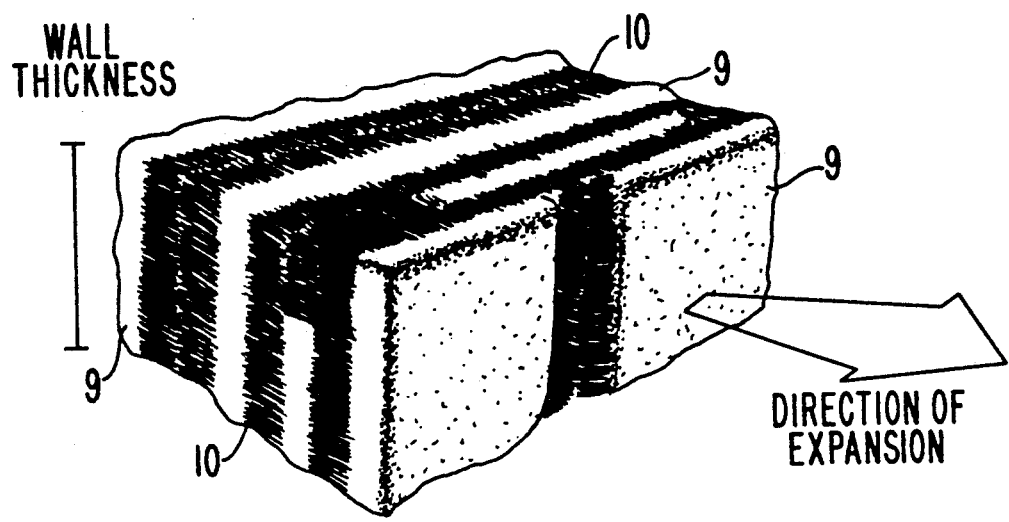
FIG. 5 is a three-dimensional view of uniaxially expanded polytetrafluoroethylene.

The fibril length of expanded PTFE is defined herein as the average of ten measurements between nodes connected by fibrils in the direction of expansion. Although FIG. 5 illustrates material expanded in one direction only, PTFE expanded in more than one direction is thought to be equally applicable to the invention. In order to measure the average fibril length of expanded PTFE, two parallel lines are drawn across a photomicrograph of about 40 to 50 times magnification of the surface of the material so as to divide the photograph into three equal areas. If the material has been uniaxially expanded, these lines are drawn in the direction of expansion (i.e., direction of orientation of fibrils). Measuring from left to right, five measurements of fibril length are made along the top line in the photograph beginning with the first node to intersect the line near the left edge of the photograph and continuing with consecutive nodes intersecting the line. Five more measurements are made along the other line from right to left beginning with the first node to intersect the line on the right hand side of the photograph. If the material is expanded in more than one direction, the lines are drawn and fibril lengths measured as above, except when a node is not attached by fibrils to a node intersecting the drawn line. In this case, the fibril length from the node to a node which creates the least angle with the drawn line is measured along the fibril's axial orientation. The ten measurements obtained by this method are averaged to obtain the average fibril length of the material.

Materials with average fibril lengths greater than about 60 microns, preferably greater than about 100 microns, ethanol bubble points of less than about 2.0 psi, preferably less than about 0.75 psi, ethanol mean flow pressure less than about 10 psi, preferably less than about 3.0 psi, and densities less than about 1 g/cc and preferably about 0.3 to about 0.1 g/cc enhance connective tissue ingrowth and are therefore preferred for use in the present invention.

When expanded PTFE is used as the porous material, it is preferred that a number of nodes 9 pass through the wall thickness of the expanded PTFE, as illustrated in FIG. 5, to provide channels for tissue ingrowth and a wall resistant to crushing. Expanded PTFE without nodes passing through its wall thickness is more easily crushed by forces of mastication, thereby decreasing the pore size, increasing the density, and compromising ingrowth. Preferably, a majority of the nodes extend across the thickness dimension of the wall. In the preferred embodiments an expanded PTFE gingival interface with a wall thickness of approximately 0.5 to 1 mm is used.

Figure 6:
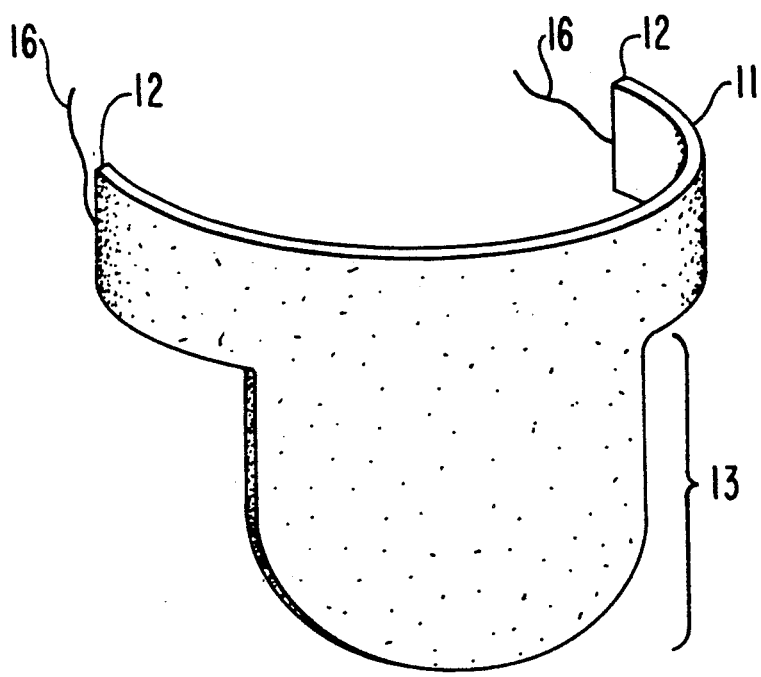
FIG. 6 is a three-dimensional view of a first preferred embodiment of the article of the invention.
Figure 7:
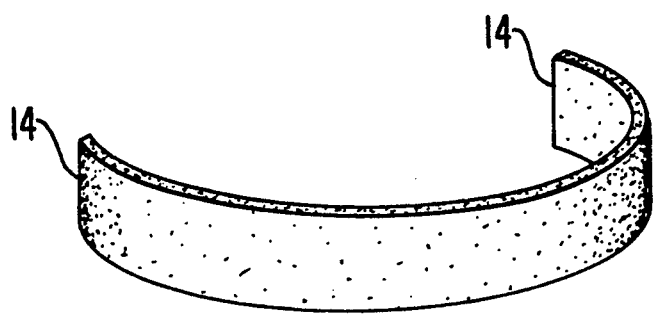
FIG. 7 is a three-dimensional view of a second preferred embodiment of the article of the invention.
Figure 8:
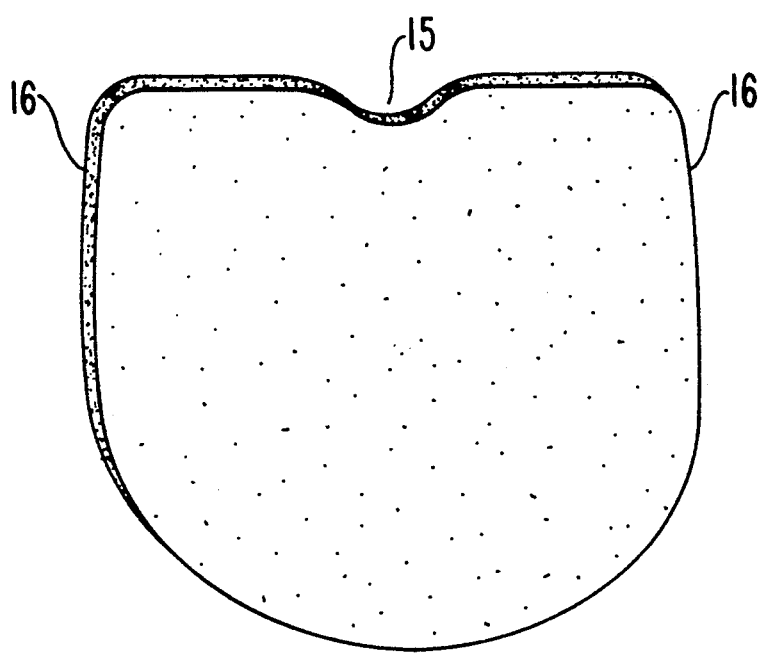
FIG. 8 is a three-dimensional view of a third preferred embodiment of the article of the invention.

The expanded PTFE articles of the present invention may be of several configurations. FIG. 6 illustrates one preferred "apron" configuration. The collar 11, of the apron is pulled snugly against the perimeter of the tooth, preferably by tying the ends 12 of the collar together with a pair of filaments 16 attached to ends 12 of the apron collar. The bib 13 of the apron is positioned coronally over bony defects adjacent to the tooth. FIG. 7 illustrates another preferred, "collar" configuration. The collar of expanded PTFE is pulled snugly against the perimeter of the tooth, preferably tying the ends 14 of the collar together using filaments not shown. FIG. 8 illustrates an additional preferred "notched patch" configuration. The notch 15 of the patch is placed snugly against the tooth, preferably by using suture material to lash the sides 16 of the patch to tissue surrounding the tooth.

The present invention also provides an article for the treatment of periodontal disease comprising a length of a porous material capable of supporting ingrowth of gingival connective tissue and preventing apical migration of gingival epithelium, said length having a biocompatible, non-porous backing on one side capable of being placed in a laminar relationship to a tooth surface. This article preferably is shaped as the "apron of FIG. 6, the "collar" of FIG. 7, or the "patch" of FIG. 8. The biocompatible, non-porous materials that comprise the backing are the same as those set forth above for use in the method for treatment of periodontal disease.

The non-porous backing may serve as a surface for placement of an adhesive to secure the article to a tooth surface. Additionally, an adhesive component may be admixed with the nonporous backing to create a mechanical seal with the tooth surface when the article is used in the method of the present invention to treat periodontal disease.

The present invention also provides an article for the treatment of periodontal disease comprising a length of porous material capable of supporting ingrowth of gingival connective tissue and preventing apical migration of gingival epithelium, said length having at least one filament attached to each of two opposite ends of the length. The filament can be used to secure the porous material to the tooth by tying the filaments around the tooth.

As stated above, the filamentous material must be biocompatible and should not serve as a conduit for bacterial invasion. Additionally, the filamentous material should not be resorbed until a sufficient time has elapsed for periodontal tissue to fill in the defect.

The porous material may be shaped as a collar, a patch or an apron, as set forth in the previous embodiment. Preferably, the porous material is shaped as an apron with the filaments serving as the "apron strings" as illustrated in FIG. 6.

Preferably, the porous material is expanded PTFE as described above. The filamentous material is preferably an expanded PTFE suture material, as also described above.

The filaments may be attached to the length of porous material by any method which provides an attachment capable of holding the porous material in place until sufficient ingrowth of periodontal tissue has occurred. Preferably, the filaments are tied or sewn to the porous material. If both the porous material and the filaments are comprised of expanded PTFE, the two may be joined by pressure and heat.

The present invention also provides an alternate method for the treatment of periodontal disease. In this alternate method, the gingival tissue is separated from a tooth surface in an area where periodontal disease is present. An article comprising a member having first and second juxtaposed surfaces meeting at a boundary, wherein the boundary is capable of at least partially encircling the perimeter of a tooth to be treated and is fixed in a laminar relationship to a portion perimeter of the tooth surface. The first surface comprises a porous, biocompatible material capable of supporting the ingrowth of gingival connective tissue and capable of preventing the apical migration of gingival epithelium. The first surface is configured so as to surround at least a portion of the perimeter of the tooth about the desired sulcus line with the porous surface abutting the gingival epithelial tissue. The second surface is substantially impermeable to oral tissues and configured to surround at least a portion of the perimeter of the tooth apical to the desired sulcus. The second surface is further positioned so as to leave at least a portion of the first surface exposed to gingival epithelial tissue in the area of the desired sulcus line. The impermeable second surface is intended to abut the gingival connective tissues. Finally, the gingival tissues are repositioned around the tooth and in contact with the article, such that at least a segment of each of the first and second portions of the article are positioned between the gingival tissue and the tooth. Preferably the gingival tissues are repositioned so that the entire article is covered by gingival tissue.

In the articles intended for use in this method, the porous materials of the first surface are contemplated to be similar to those discussed in detail in connection with the first method for treatment of periodontal disease discussed previously. In particular, it is preferred that the porous material be expanded PTFE. Materials with average fibril lengths greater than about 60 microns, preferably greater than about 100 microns, ethanol bubble points of less than about 2.0 psi, preferably less than about 0.75 psi, ethanol mean flow pressure less than about 10 psi, preferably less than about 3.0 psi, and densities less than about 1 g/cc and preferably about 0.3 to about 0.1 g/cc enhance connective tissue ingrowth and are therefore preferred for use in the present invention. It is also preferred that a number of nodes pass through the wall thickness of the expanded PTFE.

The second, impermeable surface of the article is intended to be a material which is substantially impermeable to oral tissues but which may or may not be permeable to various body fluids. In this regard, if the material of the second portion is permeable to any body fluids, it has been found that GORE-TEX ® Surgical Membrane available from W. L. Gore & Associates, Inc. performs satisfactorily.

Various materials are contemplated for use in the construction of the second surface of the article. These materials include, but are not limited to, any of the porous biocompatible materials listed above made substantially impermeable to oral tissues. It should be noted that the impermeable materials should be biocompatible in the sense that they do not cause inflammation of the oral tissues or react adversely with tissues to inhibit the healing process.

Various lamination methods might be employed to join the material forming the second surface of the article to the materials forming the first surface. Biocompatible adhesives including, but not limited to, polyurethanes or silicones may be used to join the two materials.

Alternatively, porous materials suitable for the first surface might be rendered impermeable to oral tissues in areas desired for the second surface by either coating or filling the desired areas with, for example, silicones or urethanes, or compressing the desired areas to make them less porous.

In a preferred embodiment, a sheet of expanded PTFE material capable of supporting gingival connective tissue ingrowth is utilized for the first and second surfaces. To construct the second surface, the PTFE is rendered impermeable to tissue ingrowth in desired areas by the application of heat and pressure. In this embodiment, the porous expanded PTFE of the first surface is an integral construction with the impermeable PTFE of the second surface. The second surface is preferably formed by the application of plates heated between about 300 and 400° C. and pressed against the porous expanded PTFE in the desired areas. In this embodiment, because the second surface is created by compressing the expanded PTFE of the first surface, no means for attachment of the first and second surface of the member are required.

The articles for use in this alternate method are placed in the area of the periodontal defect as set forth above, with care being taken to ensure that the first, porous surface of the article is placed coronal to the second, impermeable surface. This article may be secured in the area of the defect, if so desired, with various biocompatible glues, sutures, filaments and the like as set forth above.

Either or both of the first and second surfaces of the articles used in conjunction with this alternate method may be backed with any of the variety of non-porous substances previously disclosed as components of the articles used in practicing the first method. As noted above, such a backing will serve to retain the open structure of the porous material of the first portion of the article and may assist in securing of the articles into the area of the defect.

The advantage of using articles of the present invention having juxtaposed first and second surfaces is that the article may be removed easily. After desired healing of periodontal tissue has taken place, the first surface of the article, which is ingrown with connective tissue and has stopped the apical migration of epithelium, is separated from the gingiva. The second surface of the article can then be removed easily, as it is substantially impermeable to tissue ingrowth.

It is generally contemplated that the article of this method will be removed from the perimeter of the tooth at about four weeks after implantation, although the article may be removed at any time the desired periodontal structures have regenerated. The article may also be kept in place indefinitely. The article inhibits apical migration of gingival epithelium while allowing regeneration of healthy periodontal tissue within the defect. Upon removal of the article, it is believed that periodontal structures will have regenerated sufficiently to provide improved periodontal health for the tooth.

It is envisioned that the article contemplated for use in this method may be of a variety of constructions. In general, this article is used in a method for the treatment of periodontal disease comprising: (a) temporarily separating the gingival tissue from a tooth surface in an area where periodontal disease is present; (b) fixing an article in a laminar relationship to a portion perimeter of a tooth surface, wherein the article comprises a member having first and second juxtaposed surfaces meeting at a boundary wherein the boundary is capable of at least partially encircling the perimeter of the tooth to be treated, said first surface comprising a porous, biocompatible material capable of supporting the ingrowth of gingival connective tissue and capable of preventing the apical migration of gingival epithelium, said first surface further configured so as to surround a portion of the perimeter of the tooth about the desired sulcus line with the porous surface abutting the gingival epithelial tissue, and said second surface being substantially impermeable to oral tissues and configured so as to surround at least a portion of the perimeter of the tooth apical to the desired sulcus line, said second surface positioned to leave at least a portion of the first surface exposed to gingival epithelial tissue in the area of the desired sulcus line and said second surface abutting the gingival connective tissue and (c) repositioning the gingival tissue around the tooth and in contact with the article, with at least a segment of the first position of the article positioned to lie between the gingival tissue to be reattached and the tooth. This article may be of laminar or integral construction, as noted above.

Figures 9, 9A:
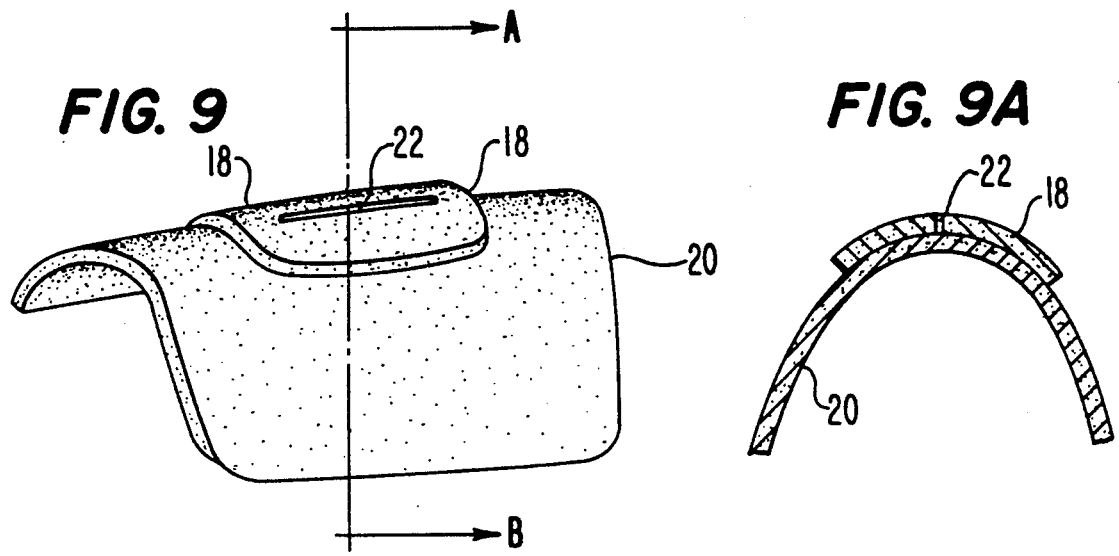
FIG. 9 is a three-dimensional view of a fourth preferred embodiment of the article of the invention wherein a first portion of the article is porous and a second portion of the article is substantially impermeable to oral tissues.
FIG. 9A is a cross-sectional view of the fourth preferred embodiment of FIG. 9 taken along line A-B.
Figures 10, 10A:
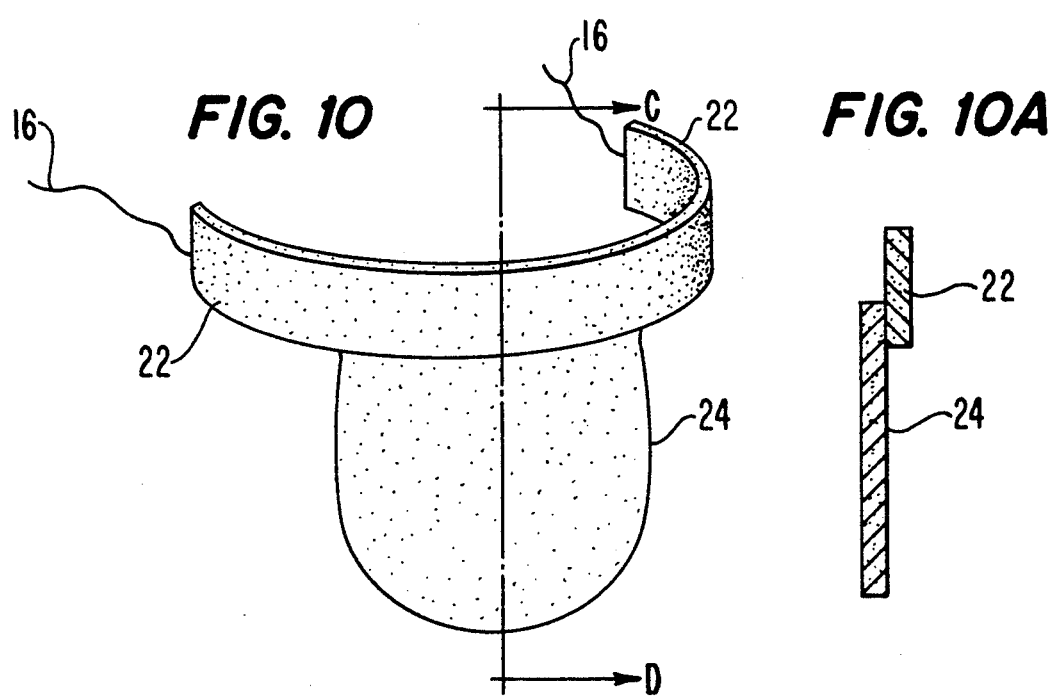
FIG. 10 is a three-dimensional view of a fifth preferred embodiment of the article of the invention wherein a first portion of the article is porous and a portion of the article is substantially impermeable to oral tissues.
FIG. 10A is a cross-sectional view of the fifth preferred embodiment of FIG. 10 taken along line C-D.

Two preferred embodiments of this article are shown in FIGS. 9 and 10. In FIG. 9, the article has a "poncho" shape. In this embodiment, the center 18 of the poncho forms the first, porous surface and the outer circumference 20 of the poncho forms the second, impermeable surface. A slit 22 or hole is rendered in the first portion 18 of the article so that the article may be placed over the tooth with portion 18 surrounding the perimeter of the tooth in the area of the desired sulcus line.

In the alternate embodiment of FIG. 10, the article has an apron shape including a collar portion defining the first porous surface 22 of the article and a bib portion defining the second, impermeable surface 24 of the article are depicted. When the article as shown in FIG. 10 is used in the above method, suture material 16 may be used to secure the article around the perimeter of the tooth.

Figure 11:
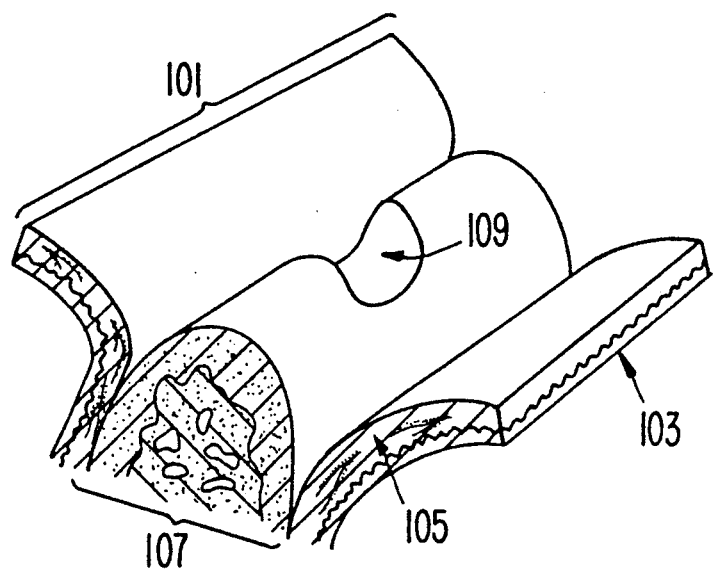
FIG. 11 is a three-dimensional view of a bony defect in the alveolar ridge wherein the mucoperiosteal flaps have been elevated thereby leaving the alveolar bone ridge exposed.
Figure 12:
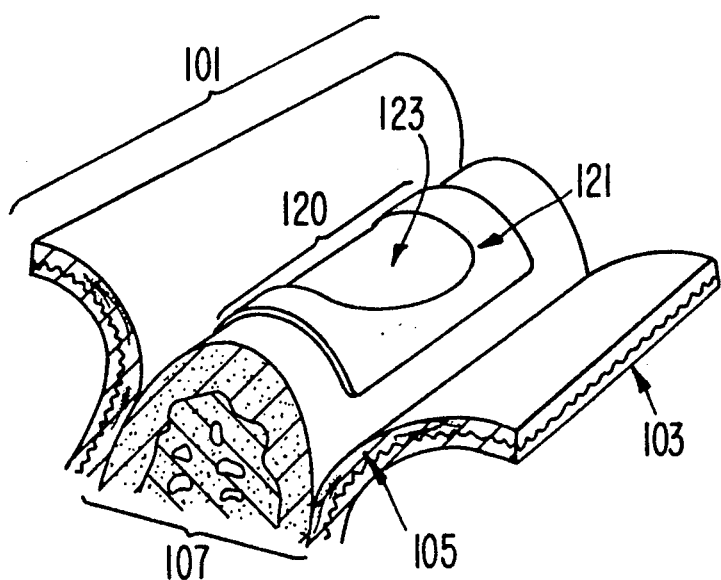
FIG. 12 is a three-dimensional view of a bony defect in the alveolar ridge similar to that of FIG. 11 repaired with the sixth embodiment of the invention.

The present invention also provides an article and method for the treatment of defects in bones, particularly in the jaw bone of the mouth. In this method, as shown in FIG. 11, the mucoperiosteal flaps 101 including the gingival epithelium 103 and gingival connective tissue 105 are separated from the alveolar ridge of the jaw bone 107 leaving exposed the bony defect 109. As shown in FIG. 12, one embodiment of the article 120 comprising a flexible, flattened member having first and second juxtaposed surfaces meeting at a boundary is positioned over the affected region of the bone and is fixed in a laminar relationship to a portion of the alveolar ridge. In the most preferred embodiment, the first surface 121 is formed of a porous, biocompatible material capable of supporting the ingrowth of connective tissue and thus preventing or retarding the migration of gingival epithelium into the defect region. This first surface is configured to be peripheral to a second surface and sized and configured so as to surround the perimeter of the defect area, and adapt closely to the contours of the bone adjacent to the defect area when the article is in place. The second surface 123 is preferably configured so that it is surrounded by the first surface. The second surface is formed of a material substantially impermeable to oral tissues and bacteria and configured to fully cover the bony defect. The second surface also creates a space (e.g. FIG. 13, space 131) between the surface and bone defect to allow bone cells to proliferate within the space without competition from cells originating from the fibrous connective tissue and epithelium. This results in filling of the defect space by viable bone tissue. Because the article will protect the defect space from epithelium, gingival connective tissue, and bacteria, bone tissue will fill the space even in the event that the article is exposed to the outside environment due to suture line dehiscence, perforation, or inability to obtain primary or complete closure of the overlying tissue. In some situations, complete closure of the tissue may not be possible (e.g., sites where a tooth is extracted leaving a gap in the soft tissue). In these cases the tissue should be closed as much as possible and stabilized with sutures. Also, allogenous, autogenous, or alloplastic materials 134 (FIG. 13A) can optionally be used to help fill the bony defect by providing a matrix for bone cell growth and/or to prevent collapse of the article into the defect space.

Figure 13:
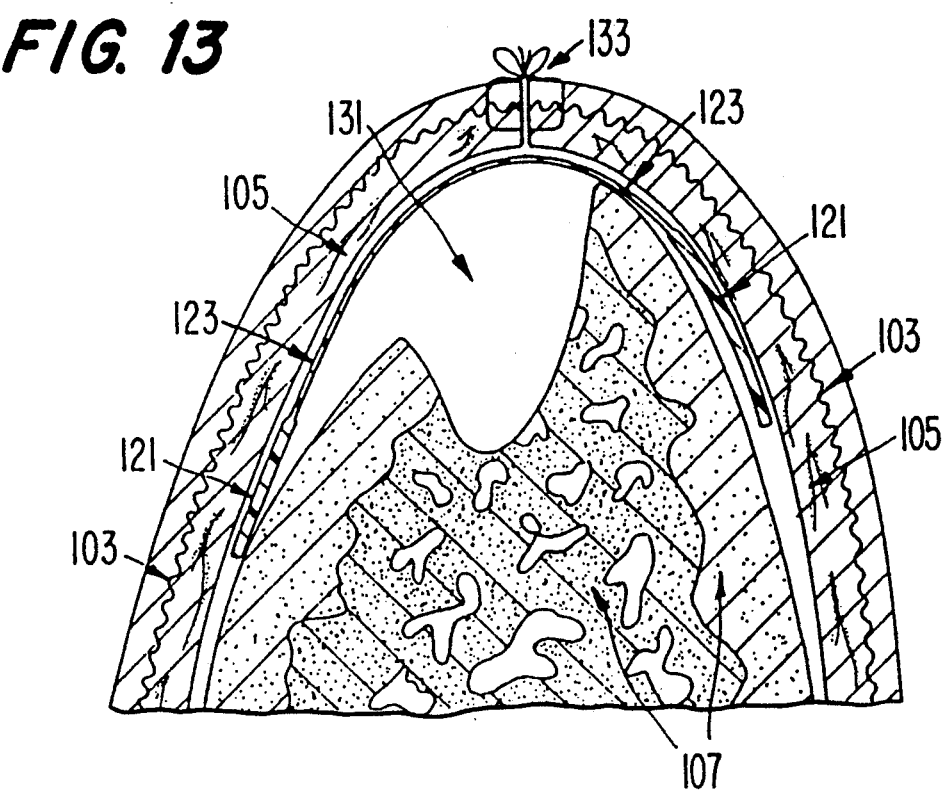
FIG. 13 is a bucco-lingual cross-sectional view of the sixth embodiment placed over the alveolar ridge bony defect and mucoperiosteal flap resutured over the article.
Figure 13A:
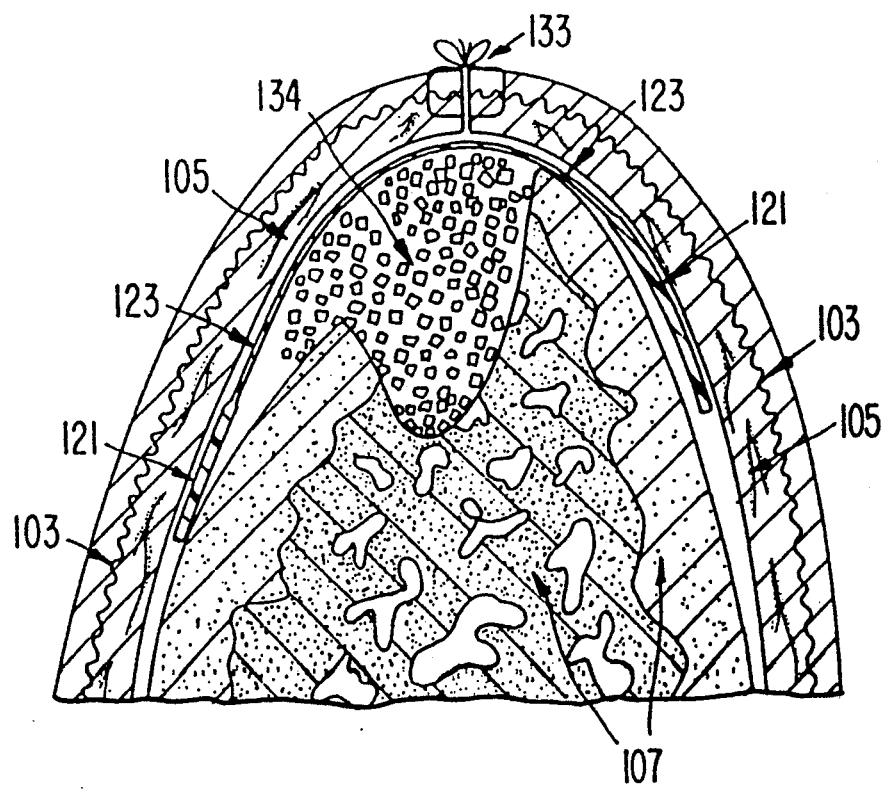
FIG. 13A is a view similar to that in FIG. 13 but showing the addition of bone filler material to the defect.
Figure 13B:
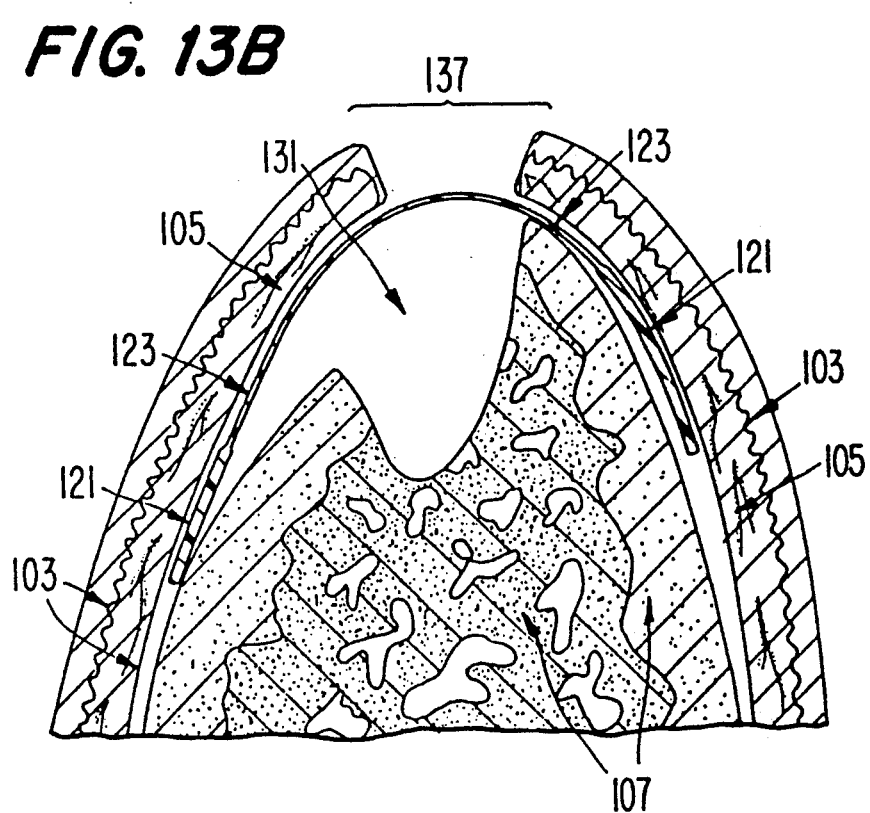
FIG. 13B is a view similar to that in FIG. 13 but showing dehiscence at the juncture of the mucoperiosteal flaps.

Finally, as shown in FIG. 13 and 13A, the mucoperiosteal flaps are repositioned so that soft tissue completely covers the implanted material 121 and 123, and the flaps are sutured closed 133. The article may be further secured in the area of the defect with various biocompatible glues, sutures, filaments and the like. However, the present invention is intended to function satisfactorily even in the event of dehiscence of the flaps at their juncture, as is depicted at 137 in FIG. 13B.

It is intended that the materials comprising either of these articles for treatment of bony defects be similar to those previously discussed in detail in connection with those methods for treatment of periodontal disease. Each of the articles may be comprised of a suitable bioresorbable, biodegradable, or hydrolyzable material so that the article dissolves over a period of time. It is most preferred, however, that the porous material be expanded PTFE which is subsequently processed to a desired microstructure such as by application of heat and pressure. Starting materials of expanded PTFE with average fibril lengths greater than about 60 microns, and preferably greater than 100 microns, densities less than 1 g/cc and preferably about 0.3 to 0.1 g/cc and a wall thickness of about 1 mm are most preferred and are subsequently compressed in certain regions to achieve desired microstructures.

When expanded PTFE is compressed by the application of heat and pressure, the microstructure of nodes and fibrils distorts so that characterization by fibril length becomes impractical. Nodes become positioned more closely together as the amount of compression is applied to the point where the material begins to approach a state where there are no void spaces between the nodes. In situations such as these, a preferred parameter used to characterize the microstructure is the internodal distance of expanded PTFE rather than fibril length. Internodal distance is defined herein as the average distance between edges of nodes in the direction of expansion based on at least 20 random measurements of internodal distance from three fields of view at 200X. Measurements were made on a Nikon medical research microscope.

One embodiment comprises a layered structure wherein a first layer having a porous surface capable of supporting ingrowth or attachment of connective tissue is arranged in laminar relationship with a second support layer which is substantially impermeable and incapable of penetration by tissues or bacteria. Here the first porous layer allows fibrous connective tissue ingrowth into the porous material or attachment along the outer surface of the porous material to inhibit or retard epithelial migration. The backing layer substantially prevents undesirable tissue and bacteria from entering the space of the bony defect and allows desirable bone cells to proliferate in the space created by the layered article.

The second embodiment, and the most preferred article, for treatment of bony defects is shown in FIGS. 14, 14A, 14B and 14C and comprises an integral member having a portion with a first porous compressed surface 121 with an average internodal distance greater than 8 microns and preferably in the range of 15-20 microns, a wall thickness of about 0.008 inches and a density of about 1.0 g/cc. The member also has a second surface 123 positioned to be central to and surrounded by the first surface which is juxtaposed in planar relationship thus forming a boundary encircling the second surface. The portion of the member forming the second surface is more greatly compressed so that it is substantially impermeable to oral tissues and bacteria; however there may be some tissue attachment topically along the second surface. The portion of the member forming the second surface preferably has an average internodal distance of less than 8 microns, a density of about 1.5 g/cc and a wall thickness of about 0.005 inches.

To construct the member portions having the representative first and second surfaces of this embodiment, application of heat and pressure to the starting expanded PTFE material similar to that previously described is used. The degree of compression to achieve each of the surfaces is controlled by the use of plates designed to be separated at predetermined distances. Similar to the previous embodiments for treatment of periodontal disease, because the two surfaces are compressed from the same starting material, no means for attachment of the first and second surface are required.

Figure 14:
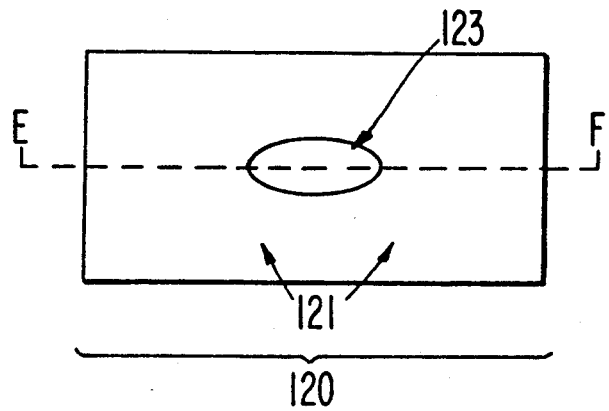
FIG. 14 is a surface view of the sixth embodiment of the invention and configured for treatment of bony defects wherein a first peripheral surface of the article is capable of supporting tissue ingrowth and a second central surface of the article that is impermeable to tissue ingrowth.
Figure 14A:
FIG. 14A is a cross-sectional view of the sixth embodiment of FIG. 14 taken along line E-F.

FIG. 14 shows the preferred shape for the article for treating a bone defect wherein the article has a rectangular shape, the center of which has a further compressed oval shaped region. FIG. 14A shows the member in cross-section with the more compressed region in the center. Alternative shapes, sizes and configurations are intended to be within the scope of the articles of this invention for treatment of bony defects.

The article used in the treatment of bony defects may be used in conjunction with bone filler materials including but not limited to autogenous, allogenous, or xenogenous bone; synthetic bone materials such as hydroxylapatite, tricalcium phosphates or polymeric materials including bioresorbable, biodegradable, or hydrolyzable sponges, particles, gels or blocks of material.

Additionally, the articles for treatment of bony defects may be used in conjunction with biologically active materials or molecules including but not limited to cell activators, antibiotics, or materials which serve as a structural framework for cellular migration such as collagen, fibronectin, or fibrin. The biologically active materials may be bound to the surface of the article, incorporated into it so that they may be released in a controlled fashion over a period of time, or placed within the bony defect space protected by the article.

Figure 14B:
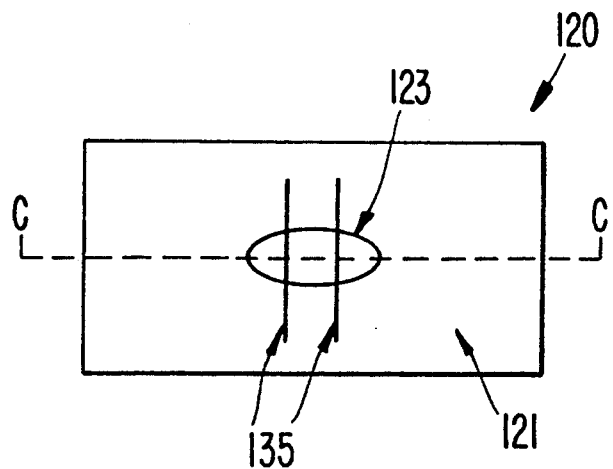
FIG. 14B shows an alternative construction similar to that in FIG. 14 but having wire reinforcements.
Figure 14C:
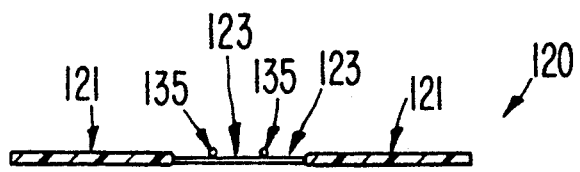
FIG. 14C is a cross-sectional view of the construction shown in FIG. 14B taken along line CC.

The articles for the treatment of bony defects may also incorporate biocompatible reinforcement components such as metallic (e.g., titanium) or polymeric wires, struts, or meshes to allow molding or shaping of the article to specific configurations or to support the article and prevent its collapse into the defect space. Such reinforcement means can, for example, comprise optional wire supports 135 at least partially attached to article 120, as shown in FIGS. 14B and 14C.

Figure 15:
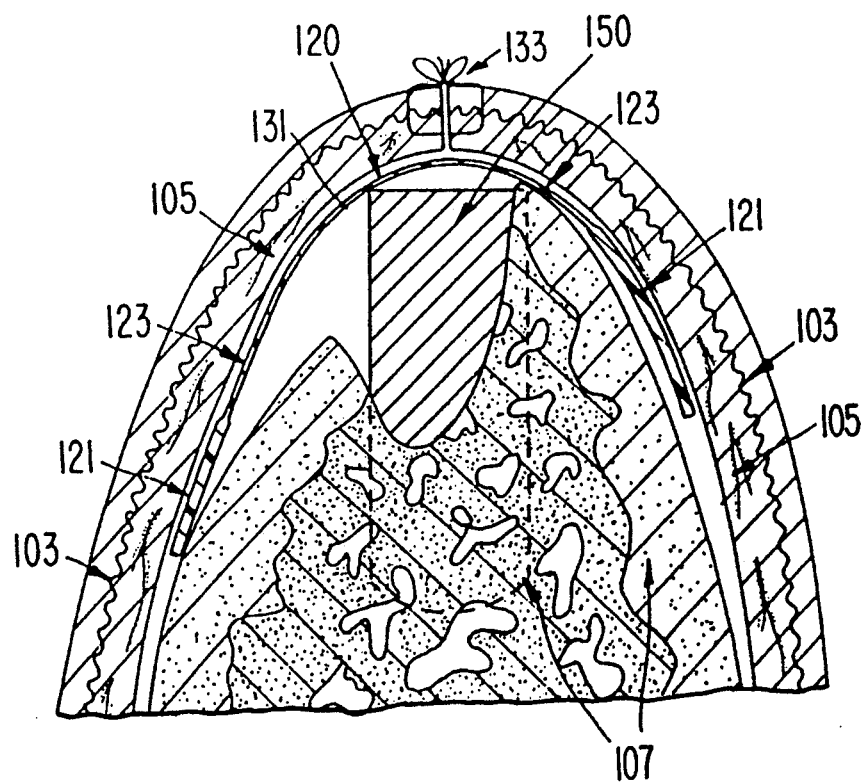
FIG. 15 is a bucco-lingual cross-sectional view of the sixth embodiment of the invention wherein a dental implant is placed within the alveolar ridge defect under-

Finally, the article may be used in conjunction with a dental implant as shown in FIG. 15 and described in Example 10 wherein the implant 150 is placed in the defect region and the article 120 of the invention is placed over it and extends over the bone ridge.

All articles of the present invention are preferably sterilized prior to insertion into a periodontal pocket or covering a bone defect. Preferably, the articles are sterilized and are contained in a package, the interior environment of which is sterile.

The following examples were designed to elucidate the teachings of the present invention and not to limit the scope of the invention. Various other modifications and equivalents of the examples will readily suggest themselves to those of ordinary skill in the art, particularly after issuance of this patent, without departing from the spirit or scope of the present invention.

EXAMPLE 1

Expanded PTFE aprons similar to those illustrated in FIG. 6 were implanted in dogs. Historically, dogs have been used to test periodontal techniques and materials (Lindhe, J. and Rylander, H., "Experimental Gingivitis in Young Dogs", *Scand. J. Dent. Res.* 83:314-326; Hilding B., "Experimental Studies on Reattachment", *Dental Practitioner*, Vol. XI, No. 10, 351-354; Ririe, C.M., Crigger, M. and Selvig, K.A., 1980 "Healing of periodontal connective tissue following surgical wounding and application of citric acid in dogs" *J. Periodontal Res.* 15:314-327; Crigger, M., Bogle, G., Nilveus, R., Egelberg, J. and Selvig, K.A., 1978 "The effect of topical citric acid application on the healing of experimental furcation defects in dogs" *J. Periodontal Research.* 13:538-549).

The expanded PTFE for the aprons was made according to the description in U.S. Pat. Nos. 4,187,390 and 3,953,566 as follows: A mixture of PTFE resin in a liquid lubricant was extruded into a tubular form. The extruded tubular form was dried for approximately 96 hours at about 300° C., which removed the lubricant. The tubular form, held at a temperature of about 295° C., was then stretched at a constant velocity along the central axis of the tube at a rate of about 75% per second until it was approximately 10 times its original length, where rate was defined as $$\frac{lf - li}{li(t)} \times 100\%$$

and lf=final length, li=initial length, and t=total time of expansion. Subsequent to stretching, the tube was restrained longitudinally and heat treated at about 375° C. for about 75 seconds. The expanded PTFE tube was then slit longitudinally through its wall and laid flat. The wall was about 1 mm thick and had nodes passing through its wall thickness. The ethanol bubble point of the material was about 0.5 psi and the ethanol mean flow pressure was about 1.0 psi. The average fibril length was about 200 microns, and the density was approximately 0.2 g/cc.

The bib and collar portion of the apron were cut from the expanded PTFE so that the collar was about 2 cm long and 2 mm wide, and the bib extended out from the collar about a centimeter. A 6-0 GORE-TEX® Expanded PTFE Suture filament, obtained from W. L. Gore & Associates, Inc., Flagstaff, Arizona, was passed through each end of the apron collar. All assembly of the apron took place in a clean room environment. The apron was sterilized prior to implantation.

At implantation, buccal and lingual periosteal flaps were reflected around dog premolar teeth. About 2 mm of crestal bone was removed circumferentially from the teeth to expose a root surface against which the aprons could be applied. Either a three wall mesial defect or a one wall buccal defect was created adjacent to the teeth using burrs and chisels. The collar of the apron was placed around the perimeter of the tooth with the bib positioned coronally over the created bony defect. The ends of the GORE-TEX® Expanded PTFE sutures were then tied together on the side of the tooth opposite the defect drawing the ends of the collars together and tightening the apron around the tooth. Any excess suture was trimmed off, and the gingival flaps were repositioned over the apron by suturing them in place. A total of five implants were placed in two dogs.

Beginning one week after surgery the implant sites were assessed clinically. After initial healing, probing revealed in all cases a healthy appearing gingiva attached to the apron forming a 2 to 3 mm deep, normal appearing sulcus. In one case, a small portion of the apron was inadvertently left exposed to the oral cavity, but all surrounding tissue appeared healthy and healed into the remainder of the apron.

Two implants, including the above mentioned case, were harvested at 20 and 30 days and assessed histologically. The expanded PTFE collar and bib, in all areas except that exposed to the oral cavity, appeared filled with connective tissue. Epithelium apparently halted its apical migration at or directly coronal to the expanded PTFE, and new bone had filled the created defects.

EXAMPLE 2

Expanded PTFE collars as illustrated in FIG. 7 backed with medical grade silicone and polyurethane were implanted in dogs. The medical grade silicone, obtained from Dow-Corning Corporation, and polyurethane, Cardiomat™ 610 obtained from Kontron Cardiovascular Inc., were applied to the expanded PTFE as a thin backing and allowed to cure. The expanded PTFE had an ethanol bubble point below about 0.75 psi, an ethanol mean flow pressure below about 1 psi, an average fibril length greater than about 100 microns, a density of about 0.3 to 0.1 g/cc, and a wall thickness of about 1 mm.

The backed, expanded PTFE was cut into strips (collars) approximately 2 mm wide and 2 cm long. The collars were sterilized and implanted in premolar sites according to the procedure detailed in Example 1 without creating defects. The silicone or polyurethane backed side of the collars was placed against the tooth, and each collar was secured around a tooth by tying its ends together with GORE-TEX® Expanded PTFE Suture. Four implants were retrieved between 19 and 32 days after surgery for histological analysis.

Probing of the implants prior to retrieval revealed a normal appearing sulcus with no inflammation and gingiva attached to the collar. Microscopic examination of the implant revealed that the polyurethane and silicone backings were in most places directly apposed to the tooth root. The expanded PTFE had filled with connective tissue and the gingival epithelium had attached to the connective tissue within the collar, apparently halting its apical migration.

EXAMPLE 3

Expanded PTFE with a urethane backing was adhered to dog teeth using a conventional glass ionomer dental cement. The expanded PTFE had an ethanol bubble point below about 0.75 psi, an ethanol mean flow pressure below about 3 psi, an average fibril length greater than about 100 microns, a density of about 0.3 to 0.1 g/cc, and a wall thickness of about 1 mm. It was backed with a mixture of glass ionomer powder, Chembond® Glass Ionomer Cement obtained from the L.D. Caulk Company, and liquid urethane, Cardiomat™ 610 Polymer. About 1.2 cc of the urethane was mixed with about 1 gram of the powder and spread in a thin coating on one side of the expanded PTFE. The backing was allowed to cure for about 24 hours. The backed, expanded PTFE was sterilized.

A small piece of the backed material approximately 1 cm×0.5 cm was adhered to the right maxillary canine root in a dog. After a gingival flap had been reflected, the glass ionomer cement was mixed according to the manufacturer's instruction and placed on the root. The backed side of the expanded PTFE was pressed into the cement before the cement had cured, and any excess cement was removed. After the adhesive had cured, the gingival flap was repositioned over the expanded PTFE and sutured in place.

Approximately one month after surgery, the implant was retrieved. Microscopic examination revealed that the backing had not remained completely attached to the tooth but that the expanded PTFE had filled with healthy, vascularized connective tissue. Gingival epithelium appeared to be attached to the connective tissue, apparently halting epithelial apical migration.

EXAMPLE 4

An apron like that described in Example 1 and two collars like those described in Example 2 were backed with a thin line of either silicone or urethane elastomer. Approximately 0.5 mm wide lines of Cardiomat™ 610 Urethane or Dow Corning medical grade silicone were forced from a syringe onto the expanded PTFE along the length of collar. The lines were placed on the side of the collar meant to fit against the tooth. The expanded PTFE collar was held slack to about 75% of its fully extended length during the application of the elastomer so that after the collar was stretched around the tooth and the ends of the collar tied together with sutures, the elastomer held the collar against the tooth as an elastic waistband holds trousers against the waist.

Each implant was sterilized and implanted in premolar sites in a dog with the bib of the apron covering a defect as described in Example 1 and the collars placed in sites with no defects. In all cases after an initial week of healing, probing revealed healthy appearing gingiva attached to the expanded PTFE forming a normal appearing sulcus adjacent to the tooth. Histological analysis showed the epithelium apparently halting its apical migration at or directly coronal to expanded PTFE filled with connective tissue. New bone had healed in the defect apical to the apron.

EXAMPLE 5

Expanded PTFE was cut into small patches approximately 12 mm×12 mm as illustrated in FIG. 8. The patches had an ethanol bubble point below about 0.75 psi, an ethanol mean flow pressure below about 3 psi, an average fibril length greater than about 100 microns, a density of about 0.3 to 0.1 g/cc, and a wall thickness of about 1 mm. After gingival flaps had been reflected, three wall mesial defects were created adjacent to the roots of two first molars in one dog and the fourth premolar in the mandible of another dog. The patches were fitted over the bony defects and conformed to the bony ridge with the root of the treated tooth resting in the notch of the patch. The gingival flaps were repositioned over the patches and sutured in place. The molar implants were retrieved 19 and 20 days after surgery, and the premolar implant was retrieved 30 days following surgery.

In all sites approximately 2 mm of expanded PTFE remained exposed to the oral cavity adjacent to the mesial aspect of the treated teeth. Histological analysis revealed that gingival tissue had filled a space between the notch of the patch and the tooth. New bone had filled the defects, and the patches had apparently inhibited the growth of gingival tissue into the defect space. The portions of expanded PTFE which had not become exposed to the oral environment were healed in with healthy, vascularized connective tissue. Epithelium had apparently halted its apical migration at the interface between the exposed and healed portions of expanded PTFE.

This treatment method was somewhat unsuccessful because gingival tissue managed to grow between the patch and the tooth surfaces. It may be possible to appose the notch of such a patch more tightly against the tooth by lashing the patch to adjacent tissue with sutures or by other suitable means. Such a patch might enable a normal sulcus to be formed around the tooth without the formation of gingival tissue between the patch and tooth or the exposure of the patch to the oral cavity. The bony defect would be filled in by the appropriate tissues of the periodontium as demonstrated in the example.

EXAMPLE 6

Expanded PTFE was adhered to a tooth using acrylic cement. The expanded PTFE had an ethanol bubble point below about 0.75 psi, an ethanol mean flow pressure below about 3 psi, an average fibril length greater than about 100 microns, a density of about 0.3 to 0.1 g/cc, and a wall thickness of about 1 mm. Concise ® and Silar ® cements were used as supplied by Dental Products/3M.

After buccal gingival flaps had been reflected from the maxillary canine of a dog, the exposed root was notched approximately 0.5 mm deep and 2 mm wide directly coronal to the bone surrounding the root from the mesial to the distal aspect of the exposed root. Silar ® paste mixed according to the manufacturer's instructions was then used to fill the notch.

A strip of the expanded PTFE, which had been sterilized, was cut approximately 2 mm wide and long enough to extend from the mesial to the distal aspect of the exposed root. Concise ® resin liquids were mixed with Concise ® paste components forming a paste which could be spread and adhered on one side of the expanded PTFE strip. The pasted side of the expanded PTFE strip was placed against the Silar ® filled notch on the root. The adhesive was allowed to set, and the gingival flap was repositioned over the expanded PTFE strip and sutured in place.

After 40 days the implant was retrieved. The expanded PTFE strip appeared well attached to the tooth. Epithelium appeared to end against the expanded PTFE, but gingival tissue surrounding and within the expanded PTFE exhibited an apparent adverse reaction to the adhesive.

An adhesive system which would bond an expanded PTFE strip to the tooth and which would be biocompatible with the oral tissue would be a more viable treatment modality.

EXAMPLE 7

Ponchos and aprons, as illustrated in FIGS. 9 and 10, were made by laminating two structures of expanded PTFE. GORE-TEX ® expanded PTFE Surgical Membrane of 0.1 mm thickness obtained from W. L. Gore & Associates, Inc. was cut into 40×25 mm rectangles to form the portion of the ponchos and aprons impermeable to tissue ingrowth. Expanded PTFE, capable of supporting the ingrowth of gingival connective tissue and preventing the migration of gingival epithelium, was cut into smaller rectangles, either 10×20 mm, 8×20 mm, or 5×20 mm.

These smaller rectangles of expanded PTFE had an ethanol bubble point below about 0.75 psi, an ethanol mean flow pressure below about 3 psi, an average fibril length greater than about 100 microns, a density of about 0.3 to 0.1 g/cc, and a wall thickness of about 0.5 mm. The smaller rectangles were laminated to the Surgical Membrane in roughly the center of the Surgical Membrane rectangles using a thin layer of either biocompatible urethane or silicone adhesive placed between the two expanded PTFE structures. The biocompatible silicone adhesive was obtained from Dow Corning Corporation, and the biocompatible urethane adhesive was a segmented polyether polyurethane obtained from Ethicon Incorporated.

After the adhesive had cured, the ponchos and aprons were steam sterilized in preparation for implantation in dogs. During surgery, buccal and lingual periosteal flaps were reflected around dog premolar teeth. Up to 7 mm of crestal bone, ligament and cementum were removed to create horizontal defects with furcation involvement. The aprons or ponchos were implanted with the Surgical Membrane material trimmed to cover the prepared defects. The gingival flaps were repositioned over the implanted material by suturing the flaps in place.

Shaping of the pieces into either ponchos or aprons took place at the time of surgery by using scalpel or sharp scissors. If a poncho was to be implanted, a slit was made through the laminate within the area of smaller rectangle of expanded PTFE. The slit was sized to fit over the crowns of the dogs' teeth and fit snugly around the tooth below the cemento-enamel junction (CEJ) The expanded PTFE capable of supporting the ingrowth of gingival connective tissue formed a collar around the tooth coronal to the Surgical Membrane portion which formed a skirt covering the defect. Aprons were formed by cutting a collar shape out of the smaller expanded PTFE rectangle and a bib shape out of the Surgical Membrane portion. The collar portions had extended tabs which were wrapped around the circumference of the tooth and drawn together against the tooth by means of absorbable suture. The collars (capable of supporting gingival connective tissue ingrowth) were placed coronal to the big portion of the aprons which covered the defects.

Approximately 20 to 30 days after surgery, a small incision around the teeth or, in some cases, a split thickness flap was used to separate tissue which had ingrown into the portion of the implants capable of supporting gingival connective tissue ingrowth. The entire implants, including collars and Surgical Membrane, were removed, and gingival tissue was reapposed to the tooth with suture where necessary.

Of eight teeth implanted, two were removed at 37 days, one was removed at 49 days, and one was removed at 61 days postsurgery for microscopic examination. The remaining implants remained in vivo for clinical evaluation.

All implant sites showed no sign of inflammation and displayed normal sulcus depths. There were no gingival pockets or other signs of apical epithelial migration. The teeth were all immobile. In one case, a tooth that had been made mobile by defect creation at the time of surgery became immobile after healing—evidence that periodontium had regenerated to support the tooth.

EXAMPLE 8

Ponchos illustrated in FIG. 9 were made with a starting material of expanded PTFE made in accordance with the methods described above. The starting material had an ethanol bubble point of below about 0.75 psi, an ethanol mean flow pressure below about 3 psi, an average fibril length greater than 100 microns, a density of about 0.3 to 0.1 g/cc, and a wall thickness of about 1 mm.

A sheet of the starting material was clamped into a metal frame to hold the material in place. The frame was positioned between two plates that had been fixed on a pneumatic press. Each plate was machined so that a rectangular central portion having dimensions of 4 mm × 12 mm was relieved such that compression of the expanded PTFE would take place peripheral to the central relieved area but not within the central relieved area. The central relieved area remained porous with an open structure. Shims were used in the press as stops to control the degree of compression. The shims were arranged to prevent the plates from contacting each other by about 0.007 inches. The plates were heated to between 300° F. and 400° F. and the expanded PTFE was compressed between the heated plates for about thirty seconds.

The resulting compressed region of expanded PTFE had a density of about 1.0 g/cc and a wall thickness of about 0.007 inches. The compressed region also had internodal distances ranging from about 5 microns to 50 microns with an estimated mean internodal distance of about 15 to 20 microns.

The resulting membrane was thus similar in shape to the poncho illustrated in FIG. 9 with a central surface of open-structured porous PTFE and a peripheral surface of compressed expanded PTFE.

Six of these ponchos were implanted into five dogs. Buccal and lingual full-thickness mucoperiosteal flaps were elevated and buccal or circumferential periodontal defects were surgically created on mandibular premolar teeth. Each poncho was placed over the teeth with the open-structure porous region adapted closely to the tooth surface at or just apical to the cemento-enamel junction. The compressed, less porous, peripheral portion of each poncho was carefully trimmed so that the defined surface completely covered the bony margins of the defect.

After placement of the poncho, the mucoperiosteal flaps were repositioned so that the soft tissue completely covered the implanted material and the flaps were sutured closed.

The dogs were sacrificed at various time intervals between one and three months post-operatively and the experimental teeth were removed en bloc for histological processing and evaluation. When analyzed histologically, it was found that the epithelium had not migrated past the porous central region of the ponchos and that the porous central regions were extensively ingrown with connective tissue and mononuclear cells. It was found also that some connective tissue had grown within the compressed peripheral region where the internodal distances were greater than 8-10 microns with more tissue ingrown where the internodal distances were greater than 15 microns. In many instances, the connective tissue penetrated the full wall thickness of this peripheral region. However, because of the ingrowth of connective tissue in this compressed peripheral region, epithelium could not migrate along the compressed region in the event that the open-structured porous region became exposed to the oral environment.

New cementum with collagen fibers was present on the previously denuded root surface and varying amounts of new bone tissue had healed into the defect space between the patch and the tooth root.

EXAMPLE 9

Expanded PTFE ponchos with integral two-part constructions were made similar to that described in Example 8. In this case, compression of the compressed peripheral region was increased by reducing the shim stop thickness to 0.005 inches. This resulted in a poncho member having a porous central region surrounded by a compressed peripheral region having a wall thickness of 0.005 inches, a density of about 1.5 g/cc and an internodal distance ranging from 0 to 40 microns with an estimated mean internodal distance of about 5 to 10 microns.

Ponchos of this type were implanted into surgically created periodontal defects on dog premolars similar to that described in Example 8. The dogs were sacrificed at various time intervals between one and three months post-operatively and the experimental teeth removed en bloc and processed for histological evaluation.

Histologically, the experimental sites showed the epithelium had halted its apical migration at or coronal to the open-structured porous central regions of the ponchos and the surface of the central porous regions of the ponchos were extensively ingrown with connective tissue and mononuclear cells.

In one case, the coronal margin of the flap was located apical to the porous region of the poncho thereby exposing this region and a portion of the compressed region to the oral environment. The epithelium was located about 1.5 to 2 mm apical to the junction between the porous region and the compressed region of the ponchos. A Brown-Brenn bacteria stain showed the presence of gram positive bacteria throughout the interstices of the open-structured porous regions and on the surface of the compressed portion of the ponchos which was exposed to the oral environment. In addition, there was localized penetration by bacteria into the compressed region exposed to the oral environment but the bacteria did not penetrate through the entire wall thickness.

Since the compressed region was more compressed than that of the material described in Example 8, the presence of connective tissue was markedly less although there was some connective tissue attachment to PTFE fibrils on the surface of this compressed region. It was noted however that this localized presence of connective tissue elements and attachment to the surface aided in retarding epithelial migration.

In the site where 2 to 3 mm of the porous region and compressed region had become exposed to the oral environment, the space between the poncho and the tooth surface coronal to the flap margin was filled with viable connective tissue which showed evidence of collagen deposition, this in spite of moderate acute inflammation. The presence of viable connective tissue indicated that bacteria were unable to permeate the compressed portion in a sufficient amount to produce infection and cause necrosis. It appeared that the larger the internodal distance, the greater the susceptibility to bacterial penetration through the wall thickness of the material.

EXAMPLE 10

Expanded PTFE patches were made with the starting material described above in Example 1. In this example, the patch did not have two juxtaposed surfaces formed by materials of different relative porosity but the entire patch was compressed so that the article implanted in each subject consisted of compressed expanded PTFE with a density of about 1.5 g/cc and a wall thickness of about 0.005 inches. The internodal distance was about 5 to 10 microns. The dimensions of each article were about 30 mm×40 mm.

The articles were implanted into six sites in humans where bony alveolar ridge defects were present and prevented or compromised placement of dental implants. Vertical incisions were made across the alveolar ridge crest mesial to the bony ridge defect and distal to sites proposed for dental implant placement. These incisions were connected on the labial side of the ridge by a horizontal incision placed apical to the mucogingival junction. Full thickness mucoperiosteal pedicle flaps were elevated and receptor holes drilled in the bone to accept dental implants. The dental implants were then placed into the prepared receptor sites. In each case a portion of the implant was not surrounded by bone because of the bony defect. In three cases, a particulate hydroxyapatite material was used as a filler in the defect to prevent the article from collapsing into the defect and space below. In the other three cases, no filler or support was provided.

The sterile patches were trimmed to the appropriate size and were draped over the bony defect and surrounding area and the dental implant. The flaps were replaced and sutured to enclose the patches.

Post-operative healing events were uneventful in 4 of the 6 sites. At one month post-operative, two of the sites showed perforation of the gingival tissue by the patches. Each article was removed by elevating the gingival tissue and peeling the patch off of the bony surface. Upon removal of each patch, it was observed that the defect space had filled with a hard, apparently calcified, bone-like tissue. The gingival tissue flaps were replaced and sutured and the sites were allowed to heal for an additional two to five months prior to placement of abutment posts and bridgework.

The remaining four patches were removed at between 1 and 3 months post-operatively. Removal was similar to the removal of similar cases with elevation of the gingival tissue and observation of the defect sites. In all cases, a hard, apparently calcified, bone-like tissue had filled each defect space. These sites were allowed to heal for an additional one to five months prior to placement of the abutment posts and bridgework. All cases were restored with bridgework and functioned assymptomatically.

In these cases, the patches were used to create and protect a bony defect space into which viable bone tissue could grow. Had there been no patch, the defect space would have filled with fibrous connective or scar tissue, thus compromising the function of the dental implant. These cases were ideal because enough space existed mesial and distal to the defect sites to prepare the pedicle flaps. This prevented any suture lines from being located directly over the articles. In many cases, it is not possible to make pedicle flaps and the incision must be placed on the ridge crest. In such instances, the patch must be capable of both limiting the migration of epithelium and protecting the defect site from bacteria.

EXAMPLE 11

Based on the results of Examples 8, 9 and 10, the following article is theorized to be the most preferable embodiment. The article has been constructed but has not been implanted in any subjects.

As Examples 8 and 9 showed, patches having regions of compressed expanded PTFE with internodal distances greater than or equal to 8 microns showed predictable connective tissue ingrowth with greater permeation as the internodal distances increased (i.e., leaving the membrane more porous) and corresponding increased potential for permeation of bacteria.

The preferred article for treating bony defects, particularly where exposure of at least a portion of the article to the oral cavity is a possibility, is comprised of an integral flexible flattened patch or member, preferably of expanded PTFE having two juxtaposed surfaces exhibiting differing average internodal spacings. To construct the member, and as shown in FIG. 14, a central region 123 of the member was compressed to a sufficient degree, such that it was made substantially impermeable to oral tissues and bacteria. The compressed region of which would be placed directly over the bony alveolar ridge defect. It has been found that compressed expanded PTFE having an internodal distance less than 8 microns and a density of 1.5 g/cc is preferred. The second region less compressed and thus more porous is peripheral to the central, highly compressed region. This peripheral region would be capable of preferential connective tissue ingrowth for inhibition of epithelial migration and should extend beyond the margins of the bony alveolar ridge defect. It has been found that compressed expanded PTFE with an internodal distance greater than about 8 microns and density of about 1.0 g/cc is preferred for the peripheral region.

To construct such a two-part member, preferential compression was used rendering a central portion that was highly compressed compared to a peripheral region with relatively less compression. This is in contrast to the patches in Examples 8 and 9 which utilized a non-compressed center region and a compressed peripheral region. Although preferential compression of an integral expanded PTFE member is the preferred method of making such a member, bonding a central portion substantially impermeable to tissue ingrowth to a peripheral more porous region capable of supporting connective tissue ingrowth could also be used.

By placing the more compressed region 123 over the bony alveolar defect as shown in FIG. 12 so that it extends 1 to 2 mm beyond the margins of the defect and the peripheral (more porous) region 121 capable of supporting tissue ingrowth extends beyond the more compressed region, a defect space can be created and protected from invasion by gingival connective and epithelial tissues and bacteria. This protected space thus creates an opportunity for bone cells to proliferate and fill the defect with viable bone tissue.

The two-part member is designed to be removed after adequate healing has occurred, generally after 1 month; however, in applications where exposure of the article is unlikely the two-part member may remain in place for the life of the patient.

It will be apparent to those skilled in the art that various modifications and variations can be made in the articles and processes of the present invention. Thus, it is intended that the present invention cover the modifications and variations of this invention provided that they come within the scope of the appended claims and their equivalents.

What is claimed is:

1. A method for the treatment of a periodontal defect comprising:
   (a) temporarily separating the gingival tissue from a tooth surface in an area where the periodontal defect is present;
   (b) fixing an article to a portion of the perimeter of the tooth surface, wherein the article comprises a flexible, flattened member having first and second juxtaposed surfaces meeting at a boundary, and wherein the member is sized for at least partially encircling the perimeter of the tooth to be treated, said first surface comprising a porous, biocompatible material configured for supporting the ingrowth of gingival connective tissue and for preventing the migration of gingival epithelium, and said second surface comprising a material substantially impermeable to oral tissues, said fixing step including the substeps of:
      (i) surrounding in a laminar relationship the porous surface about a portion of the perimeter of the tooth immediately apical to the desired sulcus line, with the porous surface abutting the gingival connective tissue, and
      (ii) at least partially covering with said second surface the periodontal defect apical to the first surface, said article being positioned so that after fixing, at least a portion of the first surface is exposed to gingival epithelial tissue along the desired sulcus line and said second surface abuts the gingival connective tissue; and
   (c) repositioning the gingival tissue around the tooth and in contact with the article, with at least a segment of the first surface of the article positioned to lie between the gingival tissue to be reattached and the tooth.

2. The method of claim 1 including the preliminary step of selecting the article to have said first surface be a biocompatible, porous material selected from the group consisting of silicones, polyurethanes, polyethylenes, polysulfones, polyacrylics, polycarboxylates, polyesters, polypropylenes, poly(hydroxyethylmethacrylates) and perfluorinated polymers.

3. The method of claim 1 including the preliminary step of selecting the article to have said first surface of said article be expanded polytetrafluoroethylene material having an average fibril length of greater than about 60 microns, an ethanol bubble point of less than about 2.0 psi, an ethanol mean flow pressure of less than about 10 psi and a density of less than about 1 g/cc.

4. The method of claim 1 wherein the fixing step includes the steps of wrapping the positioned article around the perimeter of the tooth and securing the wrapped article to itself with sutures.

5. The method of claim 1 wherein the fixing step includes the step of suturing the positioned article to the surrounding gingival tissue for securing the article in relation to said periodontal defect.

6. The method of claim 1 wherein said article has at least one filament attached to each of at least two opposite ends, and wherein said fixing step includes the step of using the filaments to tie said article around said tooth.

7. The method of claim 1 wherein said article is in the shape of a poncho including a slit formed in said first surface, said fixing step including the step of placing the poncho over the tooth with the tooth protruding through the slit.

8. The method of claim 1 wherein said article is in the shape of an apron including a collar portion defining said first surface, said fixing step including the step of placing the collar portion surrounding at least a portion of the perimeter of the tooth.

9. The method of claim 1 further including the step of applying a topical antibiotic to the periodontal pocket prior to positioning of the porous material.

10. The method of claim 1 further including the step of removing diseased gingival and epithelial tissue prior to fixing said porous material to said tooth.

11. An article for the treatment of a periodontal defect by promoting gingival tissue attachment about a desired sulcus line comprising a flexible, flattened member having first and second juxtaposed surfaces meeting at a boundary wherein said member is adapted to at least partially encircle the perimeter of the tooth to be treated, said first surface comprising a porous, biocompatible material configured for supporting ingrowth of gingival connective tissue and for preventing the migration of gingival epithelium, and configured to surround at least a portion of the perimeter of the tooth immediately apical to the desired sulcus line with the porous first surface abutting the gingival connective tissue, said second surface comprising a material substantially impermeable to oral tissues and configured to surround at least a portion of the perimeter of the tooth apical to the first surface and at least partially cover the periodontal defect.

12. The article of claim 11 wherein said first surface of said article is defined by a biocompatible, porous material selected from the group consisting of silicones, polyurethanes, polyethylenes, polysulfones, polyacrylics, polycarboxylates, polyesters, polypropylenes, poly(hydroxyethylmethacrylates) and perfluorinated polymers.

13. The article of claim 11 wherein said member is in the shape of a poncho including a slit formed in said first surface.

14. The article of claim 11 wherein said member is in the shape of an apron having a collar portion defining said first surface and a bib portion defining said second surface.

15. The article of claim 11 wherein the materials defining said first and second surfaces are integrally formed.

16. The article of claim 11 wherein the materials defining said first and second surfaces are arranged in laminar construction.

17. The article of claim 11 wherein the material defining said first porous surface is expanded polytetrafluoroethylene.

18. The article of claim 17 wherein said expanded polytetrafluoroethylene material defining said first surface has an average fibril length of greater than about 60 microns, an ethanol bubble point of less than about 2.0 psi, an ethanol mean flow pressure of less than about 10 psi and a density of less than about 1 g/cc.

19. The article of claim 18 wherein said expanded polytetrafluoroethylene material has an average fibril length of greater than about 100 microns, an ethanol bubble point of less than about 0.75 psi, an ethanol mean flow pressure of less than about 3.0 psi and a density of about 0.3 to about 0.1 g/cc.

20. The article of claim 11 wherein said second surface is compressed expanded polytetrafluoroethylene.

21. The article of claim 11 wherein said article has a biocompatible non-porous backing.

22. The article of claim 21 wherein said non-porous backing is polyurethane.

23. The article of claim 21 wherein said non-porous backing is silicone.

24. The article of claim 11 wherein a biologically active substance is incorporated into said article.

25. The article of claim 21 wherein said non-porous backing contains an adhesive component.

26. The article of claim 25 wherein said adhesive component comprises a glass ionomer powder and urethane.

27. The article of claim 11 wherein said second surface of said article is selected from the group consisting of silicones, polyurethanes, polyethylenes, polysulfones, polyacrylics, polycarboxylates, polyesters, polypropylenes, poly(hydroxyethylmethacrylates) and perfluorinated polymers.

28. A method for treatment of a periodontal defect comprising:
(a) temporarily separating the gingival tissue from a tooth surface in an area where the periodontal defect is present;
(b) fixing to at least a portion of the perimeter of the tooth surface, a flexible, flattened article comprising a biocompatible, porous material configured for supporting ingrowth of gingival connective tissue and for preventing apical migration of gingival epithelium, in a laminar relationship to at least a portion of the perimeter of the tooth about the desired sulcus line, said fixing step including the substeps of at least partially covering the periodontal defect apical to the desired sulcus line, and positioning said article so as to be exposed to the gingival connective tissues; and
(c) repositioning the gingival tissue around the tooth and in contact with said article, with at least a portion of said article positioned to lie between the gingival tissue and said tooth.

29. The method of claim 28 including the preliminary step of selecting the article to have said biocompatible, porous material be selected from the group consisting of silicones, polyurethanes, polyethylenes, polysulfones, polyacrylics, polycarboxylates, polyesters, polypropylenes, poly(hydroxyethylmethacrylates) and perfluorinated polymers.

30. The method of claim 28 including the preliminary step of selecting the article to have said porous material be expanded polytetrafluoroethylene having an average fibril length greater than 60 microns, an ethanol bubble point of less than about 2.0 psi, an ethanol mean flow pressure of less than about 10 psi and a density of less than about 1 g/cc.

31. The method of claim 28 wherein said fixing step includes the steps of wrapping said article around the perimeter of the tooth and securing said article to itself with sutures.

32. The method of claim 27 wherein said fixing step includes positioning said article in relation to the periodontal defect and suturing said article to the surrounding gingival tissue.

33. The method of claim 28 wherein said article has at least one filament attached to each of at least two opposite ends, said fixing step including the step of using said filaments to tie said porous material around said tooth.

34. The method of claim 27 wherein said article is in the shape of an apron, said fixing step including placing a portion surrounding of said apron to surround at least a portion of the perimeter of the tooth.

35. The method of claim 28 wherein said article is in the shape of a collar.

36. The method of claim 28 wherein said article is in the shape of a patch having a notch at one edge thereof, said fixing step including the step of abutting the notch against the tooth.

37. The method of claim 28 including the step of applying a topical antibiotic to the article prior to the fixing step.

38. The method of claim 28 including the step of removing diseased gingival and epithelial tissue prior to fixing said article to said tooth.

39. An article for the treatment of a periodontal defect comprising a length of flexible material having a longitudinally continuous porous surface configured for supporting ingrowth of gingival connective tissue and for preventing the migration of gingival epithelium, said length having a flattened, biocompatible surface opposing said porous surface, and means for fixing said flattened surface in a laminar relationship to a tooth surface.

40. The article of claim 39 wherein said porous surface is defined by a biocompatible material selected from the group consisting of silicones, polyurethanes, polyethylenes, polysulfones, polyacrylics, polycarboxylates, polyesters, polypropylenes, poly(hydroxyethyl)methacrylates, and perfluorinated polymers.

41. The article of claim 39 wherein said porous material is expanded polytetrafluoroethylene.

42. The article of claim 41 wherein said expanded polytetrafluoroethylene has an average fibril length of greater than about 60 microns, an ethanol bubble point of less than about 2.0 psi, an ethanol mean flow pressure of less than about 10 psi and a density of less than about 1 g/cc.

43. The article of claim 42 wherein said polytetrafluoroethylene has an average fibril length of greater than about 100 microns, an ethanol bubble point of less than about 0.75 psi, an ethanol mean flow pressure of less than about 3.0 psi and a density of about 0.3 to about 0.1 g/cc.

44. The article of claim 39 wherein said flattened surface comprises a non-porous backing, and wherein said non-porous backing is polyurethane.

45. The article of claim 39 wherein said flattened surface comprises a non-porous backing, and wherein said non-porous backing is silicone.

46. The article of claim 39 wherein said length is in the shape of a collar.

47. The article of claim 39 wherein said length is in the shape of a patch.

48. The article as in claim 39 wherein said length is in the shape of an apron.

49. An article for the treatment of a periodontal defect comprising a length of flexible, flattened porous material configured for supporting ingrowth of gingival connective tissue and for preventing migration of gingival epithelium, said length having at least one filament attached to each of at least two opposite ends.

50. The article of claim 49 wherein said porous material is biocompatible, porous material selected from the group consisting of silicones, polyurethanes, polyethylenes, polysulfones, polyacrylics, polycarboxylates, polyesters, polypropylenes, poly(hydroxyethyl)methacrylates, and perfluorinated polymers.

51. The article of claim 49 wherein said porous material is expanded polytetrafluoroethylene.

52. The article of claim 51 wherein said polytetrafluoroethylene has an average fibril length of greater than about 60 microns, an ethanol bubble point of less than abut 2.0 psi, an ethanol mean flow pressure of less than about 10 psi and a density of less than about 1 g/cc.

53. The article of claim 52 wherein said polytetrafluoroethylene has an average fibril length of greater than about 100 microns, an ethanol bubble point of less than about 0.75 psi, an ethanol mean flow pressure of less than about 3.0 psi and a density of about 0.3 to about 0.1 g/cc.

54. The article of claim 49 having a non-porous backing affixed to said flattened material, said flattened material and said affixed backing configured to be fixed in a laminar relationship to the tooth surface where connective tissue reattachment is desired.

55. The article of claim 49 wherein said filaments are expanded polytetrafluoroethylene.

56. The article of claim 49 wherein said article has been sterilized and is contained in a package, the interior environment of which is also sterile.

57. The article as in claim 49 wherein said length is in the shape of a collar.

58. The article of claim 49 wherein said length is in the shape of a patch.

59. The article as in claim 49 wherein said length is in the shape of an apron.

60. An article of manufacture for use in prosthetic implants for treating tissue defects and capable of supporting preferential tissue ingrowth, the article comprising a flexible, flattened member of one or more biocompatible materials having portions defining first and second juxtaposed surfaces meeting at a boundary, said first surface being configured to at least partially surround the defect and being capable of supporting the ingrowth or attachment of connective tissue and said second surface being configured to at least partially cover the defect and being substantially impermeable to tissue ingrowth and bacteria.

61. The article as in claim 60 wherein said member is contiguous across said boundary.

62. The article as in claim 60 wherein said member portion defining said first surface is expanded porous polytetrafluoroethylene.

63. An article of manufacture for use in prosthetic implants and capable of supporting preferential connective tissue ingrowth and/or attachment for treating bone defects, the article comprising a flexible, flattened member having respective portions defining first and second juxtaposed surfaces, said first surface at least partially surrounding said second surface, wherein said first surface is capable of supporting connective tissue ingrowth and/or attachment and wherein the relative permeability of said first and said second surfaces to connective tissue ingrowth and bacteria is different.

64. The article of claim 63 wherein said first surface totally surrounds said second surface, and wherein said second surface is centrally located with respect to said first surface.

65. The article of claim 63 wherein said first surface is capable of supporting connective tissue ingrowth or attachment and wherein said second surface is substantially impermeable to bacteria and connective tissue ingrowth.

66. The article of claim 63 wherein said member is an integral member.

67. The article of claim 63 further including means for supporting said member in conforming relation to the bone in the vicinity of the defect.

68. The article of claim 67 wherein said support means includes wire means embedded in said member.

69. The article of claim 68 wherein said wire means includes titanium wire.

70. The article of claim 63 wherein said first surface is formed by an expanded polytetrafluoroethylene material having an internodal distance of greater than or equal to 8 microns and a density of about 1.0 g/cc.

71. The article of claim 70 wherein the material forming said second surface is expanded polytetrafluoroethylene having an internodal distance of less than about 8 microns and a density of about 1.5 g/cc.

72. The article of claim 71 wherein said member is integrally formed, and wherein the thickness of said member portions forming said first and second surfaces is about 0.008 inches and about 0.005 inches, respectively.

73. The article of claim 63 wherein a biologically active substance is releasably contained in said member.

74. The article of claim 63 wherein at least the member portions having the higher relative permeability to connective tissue ingrowth is made from one or more biocompatible materials selected from the group consisting of silicones, polyurethanes, polyethylenes, polysulfones, polyacrylics, polycarboxylates, polyesters, polypropylenes, poly(hydroxyethyl)methacrylates, and perfluorinated polymers.

75. A method of treating a defect in a bone at least partially covered by soft tissue, the method including the steps of:
   a) temporarily separating the soft tissue from the bone in the area of the defect;
   b) fixing in laminar relationship to cover the bone defect an article having a surface capable of supporting connective tissue ingrowth, said fixing step including the step of orienting the article to oppose the bone surrounding the defect; and
   c) repositioning the previously separated soft tissue over the article.

76. The method of claim 75 including the preliminary step of selecting a member formed from expanded polytetrafluoroethylene material and having at least an article portion with an internodal distance of greater than about 8 microns, said fixing step including the step of opposing in laminar relationship the bone surrounding the defect with said article portion.

77. The method of claim 75 including the step of adding bone filler to the defect prior to the fixing step.

* * * * *

UNITED STATES PATENT AND TRADEMARK OFFICE
CERTIFICATE OF CORRECTION

PATENT NO. : 5,032,445
DATED : July 16, 1991
INVENTOR(S) : SCANTLEBURY et al.

It is certified that error appears in the above-identified patent and that said Letters Patent is hereby corrected as shown below:

Claim 32, col. 28, line 30, change "claim 27" to --claim 28--.

Claim 34, col. 28, line 38, change "claim 27" to --claim 28--; and line 40, delete "surrounding".

Signed and Sealed this

Twenty-second Day of February, 1994

Attest:

BRUCE LEHMAN

Attesting Officer

Commissioner of Patents and Trademarks